United States Patent
Burwinkel et al.

(10) Patent No.: US 11,638,563 B2
(45) Date of Patent: May 2, 2023

(54) PREDICTIVE FALL EVENT MANAGEMENT SYSTEM AND METHOD OF USING SAME

(71) Applicant: Starkey Laboratories, Inc., Eden Prairie, MN (US)

(72) Inventors: Justin R. Burwinkel, Eden Prairie, MN (US); Buye Xu, Sammamish, WA (US); Jason A. Galster, Studio City, CA (US); Peter J. Tetrick, Chaska, MN (US); Sourav K. Bhunia, Shoreview, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 109 days.

(21) Appl. No.: 16/725,766

(22) Filed: Dec. 23, 2019

(65) Prior Publication Data

US 2020/0205746 A1    Jul. 2, 2020

Related U.S. Application Data

(60) Provisional application No. 62/785,295, filed on Dec. 27, 2018.

(51) Int. Cl.
*A61B 5/00*    (2006.01)
*G16H 50/30*   (2018.01)
(Continued)

(52) U.S. Cl.
CPC ............ *A61B 5/7275* (2013.01); *A61B 5/112* (2013.01); *A61B 5/1117* (2013.01);
(Continued)

(58) Field of Classification Search
None
See application file for complete search history.

(56) References Cited

U.S. PATENT DOCUMENTS

| 5,913,310 A | 6/1999 | Brown |
| 6,186,145 B1 | 2/2001 | Brown |

(Continued)

FOREIGN PATENT DOCUMENTS

| EP | 0799597 | 10/1997 |
| EP | 1229508 | 8/2002 |

(Continued)

OTHER PUBLICATIONS

Barber & Stockwell, "Manual of Electronystagmography," 1980, C.V. Mosby Company, St. Louis, Missouri, Cover page, copyright page, and table of contents total of 3 pages.
(Continued)

*Primary Examiner* — Shirley X Jian
(74) *Attorney, Agent, or Firm* — Pauly, DeVries Smith & Deffner LLC

(57) ABSTRACT

Various embodiments of a predictive fall event management system and a method of using such system are disclosed. The system includes a body-worn device and a controller operatively connected to the body-worn device. The controller is adapted to receive physiological data representative of a physiological characteristic of a wearer of the body-worn device over a monitoring time period; receive contextual data representative of context information of the wearer over the monitoring time period; and determine one or more future physiological states or contextual states based at least in part on one or more of the physiological data and the contextual data. The controller is further adapted to determine, for a future time, whether a fall condition is satisfied based upon the one or more future physiological states or contextual states and generate a fall prevention output responsive to satisfaction of the fall condition.

20 Claims, 6 Drawing Sheets

(51) Int. Cl.
*A61B 5/11* (2006.01)
*G08B 21/04* (2006.01)
(52) U.S. Cl.
CPC ....... *G08B 21/043* (2013.01); *G08B 21/0446* (2013.01); *G16H 50/30* (2018.01)

(56) References Cited

U.S. PATENT DOCUMENTS

| | | |
|---|---|---|
| 6,326,918 B1 | 12/2001 | Stewart |
| 6,475,161 B2 | 11/2002 | Teicher et al. |
| 6,568,396 B1 | 5/2003 | Anthony |
| 6,609,523 B1 | 8/2003 | Anthony |
| 6,647,257 B2 | 11/2003 | Owensby |
| D487,409 S | 3/2004 | Philipson |
| 6,758,218 B2 | 7/2004 | Anthony |
| 6,816,878 B1 | 11/2004 | Zimmers et al. |
| 6,836,667 B1 | 12/2004 | Smith |
| 7,007,327 B2 | 3/2006 | Ogawa et al. |
| 7,139,820 B1 | 11/2006 | Otoole, Jr. et al. |
| 7,282,031 B2 | 10/2007 | Hendrich |
| 7,294,107 B2 | 11/2007 | Simon et al. |
| 7,411,493 B2 | 8/2008 | Smith |
| 7,450,954 B2 | 11/2008 | Randall |
| 7,490,611 B2 | 2/2009 | Bromwich |
| 7,602,930 B2 | 10/2009 | Kasztelan |
| 7,612,681 B2 * | 11/2009 | Azzaro ................ G16H 50/30 340/573.4 |
| 7,682,308 B2 | 3/2010 | Hendrich |
| 7,742,774 B2 | 6/2010 | Oh et al. |
| 7,892,180 B2 | 2/2011 | Epley |
| 7,899,621 B2 | 3/2011 | Breed et al. |
| 8,092,398 B2 | 1/2012 | Weinberg et al. |
| 8,150,044 B2 | 4/2012 | Goldstein et al. |
| 8,162,846 B2 | 4/2012 | Epley |
| 8,169,938 B2 | 5/2012 | Duchscher et al. |
| 8,308,665 B2 | 11/2012 | Harry et al. |
| 8,442,245 B2 | 5/2013 | Wurzbacher et al. |
| 8,452,273 B1 | 5/2013 | Khomenko et al. |
| 8,494,507 B1 | 7/2013 | Tedesco et al. |
| 8,559,914 B2 | 10/2013 | Jones |
| 8,585,589 B1 | 11/2013 | Cinberg |
| 8,652,040 B2 | 2/2014 | Leboeuf et al. |
| 8,737,951 B2 | 5/2014 | Jones et al. |
| 9,049,558 B2 | 6/2015 | Jones et al. |
| 9,149,222 B1 | 10/2015 | Zets et al. |
| 9,167,356 B2 | 10/2015 | Higgins et al. |
| 9,179,862 B2 | 11/2015 | Stergiou et al. |
| 9,216,132 B2 | 12/2015 | Aoki et al. |
| D747,554 S | 1/2016 | Daniel |
| 9,226,706 B2 | 1/2016 | Uehara et al. |
| 9,313,585 B2 | 4/2016 | Lunner |
| 9,392,966 B2 * | 7/2016 | Ten Kate ............ A61B 5/6831 |
| 9,414,784 B1 | 8/2016 | Berme et al. |
| 9,426,582 B2 | 8/2016 | Pontoppidan |
| 9,452,101 B2 | 9/2016 | Tomlinson et al. |
| 9,605,390 B2 | 3/2017 | Penland |
| 9,607,498 B2 * | 3/2017 | Osorio ................ A61B 5/746 |
| 9,848,273 B1 | 12/2017 | Helwani et al. |
| 9,877,668 B1 | 1/2018 | Sarkar et al. |
| 9,918,663 B2 | 3/2018 | Singhatat |
| 9,936,916 B2 | 4/2018 | Sahin |
| 9,999,377 B2 * | 6/2018 | Osorio ................ A61B 5/1117 |
| 10,015,579 B2 | 7/2018 | Boesen |
| 10,140,833 B1 * | 11/2018 | Jacobson ............ G16H 50/30 |
| 10,149,798 B2 | 12/2018 | Roth |
| 10,178,970 B2 | 1/2019 | Oddsson et al. |
| 10,242,590 B2 | 3/2019 | Yu |
| 10,258,257 B2 * | 4/2019 | Greene ................ G16H 40/63 |
| 10,262,517 B2 * | 4/2019 | Bobda ............ G08B 13/19613 |
| 10,271,790 B2 | 4/2019 | Lee |
| 10,319,209 B2 * | 6/2019 | Carlton-Foss ...... G06N 20/00 |
| 10,624,559 B2 * | 4/2020 | Bhunia ................ A61B 5/7455 |
| 11,277,697 B2 | 3/2022 | Burwinkel et al. |
| 2002/0188217 A1 | 12/2002 | Farwell |
| 2004/0234933 A1 | 11/2004 | Dawson et al. |
| 2005/0046576 A1 | 3/2005 | Julian et al. |
| 2005/0240378 A1 | 10/2005 | Smith et al. |
| 2005/0273017 A1 | 12/2005 | Gordon |
| 2006/0251334 A1 | 11/2006 | Oba et al. |
| 2006/0282021 A1 | 12/2006 | Devaul et al. |
| 2007/0177103 A1 | 8/2007 | Migliaccio et al. |
| 2007/0197881 A1 | 8/2007 | Wolf et al. |
| 2007/0200927 A1 | 8/2007 | Krenik |
| 2008/0021731 A1 | 1/2008 | Rodgers |
| 2008/0129518 A1 | 6/2008 | Carlton-Foss |
| 2008/0146890 A1 | 6/2008 | Leboeuf et al. |
| 2008/0186189 A1 * | 8/2008 | Azzaro ................ G16H 15/00 340/573.7 |
| 2009/0058660 A1 | 3/2009 | Torch |
| 2009/0240170 A1 * | 9/2009 | Rowley ............... A61B 5/6831 600/595 |
| 2009/0240172 A1 | 9/2009 | Fernandez et al. |
| 2009/0299622 A1 | 12/2009 | Denaro |
| 2009/0322513 A1 | 12/2009 | Hwang et al. |
| 2010/0010832 A1 | 1/2010 | Boute et al. |
| 2010/0049095 A1 * | 2/2010 | Bunn ..................... G16H 40/60 600/595 |
| 2010/0075806 A1 | 3/2010 | Montgomery |
| 2010/0141439 A1 | 6/2010 | Lunner |
| 2010/0179389 A1 | 7/2010 | Moroney, III et al. |
| 2012/0092156 A1 | 4/2012 | Tran |
| 2012/0101411 A1 | 4/2012 | Hausdorff et al. |
| 2012/0119904 A1 | 5/2012 | Coleman et al. |
| 2012/0219180 A1 | 8/2012 | Mehra |
| 2012/0304767 A1 | 12/2012 | Howard et al. |
| 2013/0065569 A1 | 3/2013 | Leipzig et al. |
| 2013/0091016 A1 | 4/2013 | Shutter |
| 2013/0135097 A1 | 5/2013 | Doezema |
| 2013/0343584 A1 | 12/2013 | Bennett et al. |
| 2013/0343585 A1 | 12/2013 | Bennett et al. |
| 2014/0002586 A1 | 1/2014 | Nourbakhsh |
| 2014/0023216 A1 | 1/2014 | Solum et al. |
| 2014/0024972 A1 * | 1/2014 | Greene ................ A61B 5/7275 600/595 |
| 2014/0031703 A1 | 1/2014 | Rayner et al. |
| 2014/0064528 A1 | 3/2014 | Flood et al. |
| 2014/0074180 A1 | 3/2014 | Heldman et al. |
| 2014/0145848 A1 * | 5/2014 | Amir ..................... G08B 21/043 702/150 |
| 2014/0148733 A1 | 5/2014 | Stone et al. |
| 2014/0257051 A1 | 9/2014 | Cam et al. |
| 2014/0266988 A1 | 9/2014 | Fisher et al. |
| 2014/0276238 A1 * | 9/2014 | Osorio ..................... A61B 5/16 600/595 |
| 2015/0018724 A1 | 1/2015 | Hsu et al. |
| 2015/0040685 A1 | 2/2015 | Nicholson et al. |
| 2015/0112162 A1 | 4/2015 | Wilmink |
| 2015/0164383 A1 | 6/2015 | Varsavsky et al. |
| 2015/0196231 A1 | 7/2015 | Ziaie et al. |
| 2015/0209212 A1 | 7/2015 | Duguid |
| 2015/0226621 A1 | 8/2015 | Zhu et al. |
| 2015/0257662 A1 | 9/2015 | Lee et al. |
| 2015/0269824 A1 | 9/2015 | Zhang |
| 2015/0319546 A1 | 11/2015 | Sprague |
| 2015/0351690 A1 | 12/2015 | Toth et al. |
| 2016/0029938 A1 | 2/2016 | Shudo |
| 2016/0033280 A1 | 2/2016 | Moore et al. |
| 2016/0070122 A1 | 3/2016 | Sales et al. |
| 2016/0100776 A1 | 4/2016 | Najafi et al. |
| 2016/0106346 A1 | 4/2016 | Benzel et al. |
| 2016/0155312 A1 * | 6/2016 | Osorio ............... G08B 21/0446 340/573.1 |
| 2016/0262608 A1 | 9/2016 | Krueger |
| 2016/0263437 A1 | 9/2016 | Kow et al. |
| 2016/0275805 A1 | 9/2016 | Reichow |
| 2016/0295978 A1 | 10/2016 | Hyde et al. |
| 2017/0000387 A1 | 1/2017 | Forth et al. |
| 2017/0006931 A1 | 1/2017 | Guez et al. |
| 2017/0007147 A1 | 1/2017 | Hasegawa |
| 2017/0055917 A1 * | 3/2017 | Stone ..................... A61B 5/1115 |
| 2017/0071532 A1 | 3/2017 | Greco |
| 2017/0112671 A1 | 4/2017 | Goldstein |
| 2017/0116846 A1 | 4/2017 | Wengrovitz et al. |
| 2017/0127196 A1 | 5/2017 | Blum et al. |

(56) References Cited

U.S. PATENT DOCUMENTS

| | | | |
|---|---|---|---|
| 2017/0140637 A1 | 5/2017 | Thurlow et al. | |
| 2017/0156965 A1 | 6/2017 | Geisinger et al. | |
| 2017/0169716 A1 | 6/2017 | Super et al. | |
| 2017/0172465 A1* | 6/2017 | Osorio | A61B 5/1117 |
| 2017/0188895 A1 | 7/2017 | Nathan | |
| 2017/0197115 A1 | 7/2017 | Cook et al. | |
| 2017/0229041 A1 | 8/2017 | Reichow et al. | |
| 2017/0273616 A1 | 9/2017 | Yang et al. | |
| 2017/0274219 A1 | 9/2017 | Ernst et al. | |
| 2017/0291065 A1 | 10/2017 | Klopman | |
| 2017/0352240 A1* | 12/2017 | Carlton-Foss | A61B 5/11 |
| 2017/0358195 A1* | 12/2017 | Bobda | G08B 13/19613 |
| 2017/0358241 A1 | 12/2017 | Wexler et al. | |
| 2017/0360364 A1 | 12/2017 | Heasman et al. | |
| 2018/0000385 A1 | 1/2018 | Heaton et al. | |
| 2018/0092572 A1 | 4/2018 | Sanchez et al. | |
| 2018/0093121 A1 | 4/2018 | Matsuura et al. | |
| 2018/0110466 A1 | 4/2018 | Ralston | |
| 2018/0132757 A1* | 5/2018 | Kong | A61B 5/1038 |
| 2018/0177436 A1* | 6/2018 | Chang | A61B 5/112 |
| 2018/0202813 A1 | 7/2018 | Belt et al. | |
| 2018/0228404 A1 | 8/2018 | Bhunia et al. | |
| 2018/0228405 A1* | 8/2018 | Burwinkle | A61B 5/0002 |
| 2018/0233018 A1* | 8/2018 | Burwinkel | G08B 21/0492 |
| 2018/0233028 A1 | 8/2018 | Rhoads et al. | |
| 2018/0234781 A1 | 8/2018 | Stewart et al. | |
| 2018/0242859 A1 | 8/2018 | Leboeuf et al. | |
| 2018/0250494 A1 | 9/2018 | Hanbury | |
| 2018/0279915 A1 | 10/2018 | Huang et al. | |
| 2018/0279919 A1 | 10/2018 | Bansbach et al. | |
| 2018/0289287 A1 | 10/2018 | Sio et al. | |
| 2018/0317837 A1 | 11/2018 | Burwinkel et al. | |
| 2018/0341582 A1 | 11/2018 | Moon et al. | |
| 2018/0343527 A1 | 11/2018 | Edwards | |
| 2019/0015046 A1 | 1/2019 | Whitehouse et al. | |
| 2019/0117121 A1 | 4/2019 | Kutina et al. | |
| 2019/0246890 A1 | 8/2019 | Kerasidis et al. | |
| 2020/0138364 A1 | 5/2020 | Fabry et al. | |
| 2020/0143703 A1 | 5/2020 | Fabry et al. | |
| 2020/0219373 A1 | 7/2020 | Stut et al. | |
| 2020/0236479 A1 | 7/2020 | Burwinkel et al. | |
| 2022/0031195 A1* | 2/2022 | Hu | A61B 5/1128 |
| 2022/0248153 A1 | 8/2022 | Burwinkel et al. | |
| 2022/0248970 A1 | 8/2022 | Burwinkel et al. | |

FOREIGN PATENT DOCUMENTS

| | | |
|---|---|---|
| EP | 1628504 | 2/2006 |
| EP | 2104366 | 9/2009 |
| EP | 2700907 | 2/2014 |
| EP | 2725818 | 4/2014 |
| EP | 3075306 | 10/2016 |
| EP | 3131027 | 2/2017 |
| EP | 1983896 | 6/2017 |
| EP | 3246888 | 11/2017 |
| EP | 3346402 | 7/2018 |
| EP | 3402218 | 11/2018 |
| EP | 3591990 | 1/2020 |
| EP | 3669765 | 6/2020 |
| WO | 2008143908 | 11/2008 |
| WO | 2009053184 | 4/2009 |
| WO | 2010046504 | 4/2010 |
| WO | 2010049543 | 5/2010 |
| WO | 2010108287 | 9/2010 |
| WO | 2012083102 | 6/2012 |
| WO | 2015164456 | 10/2015 |
| WO | 2016088027 | 6/2016 |
| WO | 2016097746 | 6/2016 |
| WO | 2016110804 | 7/2016 |
| WO | 2016123129 | 8/2016 |
| WO | 2017023864 | 2/2017 |
| WO | 2018127851 | 7/2018 |
| WO | 2018147942 | 8/2018 |
| WO | 2018147943 | 8/2018 |
| WO | 2018148713 | 8/2018 |
| WO | 2018223505 | 12/2018 |
| WO | 2019073473 | 4/2019 |
| WO | 2019086997 | 5/2019 |
| WO | 2020097353 | 5/2020 |
| WO | 2020097355 | 5/2020 |
| WO | 2020124022 | 6/2020 |
| WO | 2020139850 | 7/2020 |
| WO | 2020206155 | 10/2020 |
| WO | 2022094089 | 5/2022 |

OTHER PUBLICATIONS

Buatois, et al., "Posturography and Risk of Recurrent Falls in Healthy Non-Institutionalized Persons Aged Over 65," Gerontology, 2006; 52(6):345-352 (8 pages).

Choi, W. J. et al., "Effect of Neck Flexor Muscle Activation on Impact Velocity of the Head During Backward Falls in Young Adults," Clinical Biomechanics 49 (2017), pp. 28-33.

Coburn, Courtney et al., "The Comfort Bud: Designed with Patients in Mind," Starkey Hearing Technologies Product Sheet, 2017 (2 pages).

Da Costa, et al., "Can Falls Risk Prediction Tools Correctly Identify Fall-Prone Elderly Rehabilitation Inpatients? A Systematic Review and Meta-Analysis," PLoS ONE, 2012; 7(7):e41061 (8 pages).

El Miedany, et al., "Falls Risk Assessment Score (FRAS): Time to Rethink," Journal of Clinical Gerontology & Geriatrics, 2011: 2011; 2(1):21-26 (6 pages).

EP Search Report dated Oct. 8, 2018 from EP App. No. 18171323.1, 10 pages.

Farrell, Lisa et al., "Vestibular Rehabilitation: An Effective, Evidence-Based Treatment," Vestibular Disorders Association 2015 (11 pages).

"Final Office Action," for U.S. Appl. No. 15/858,630 dated Mar. 21, 2019 (15 pages).

"Final Office Action," for U.S. Appl. No. 15/858,680 dated May 21, 2020 (11 pages).

"Final Office Action," for U.S. Appl. No. 15/895,311 dated Jul. 17, 2020 (18 pages).

Hendrich, Ann et al., "Hospital Falls: Development of a Predictive Model for Clinical Practice," Applied Nursing Research, vol. 8, No. 3 (Aug.), 1995: pp. 129-139 (11 pages).

Hendrich, Ann L. et al., "Validation of the Hendrich II Fall Risk Model: A Large Concurrent Case/Control Study of Hospitalized Patients," Applied Nursing Research, vol. 16, No. 1 (Feb.), 2003: pp. 9-21 (13 pages).

Horak, "Postural Orientation and Equilibrium: What do we Need to Know About Neural Control of Balance to Prevent Falls?," Age and Ageing, 2006; 35-S2:ii7-ii11 (5 pages).

Howcroft, et al., "Review of Fall Risk Assessment in Geriatric Populations using Inertial Sensors," J Neuroeng Rehab, 2013; 10:91 (12 pages).

Howcroft, et al., "Understanding Dynamic Stability From Pelvis Accelerometer Data and the Relationship to Balance and Mobility in Transtibial Amputees," Gait Posture, 2015; 41(3): 808-812 (5 pages).

"International Preliminary Report on Patentability," for PCT Application No. PCT/US2017/069026 dated Aug. 22, 2019 (9 pages).

"International Preliminary Report on Patentability," for PCT Application No. PCT/US2017/0690365 dated Aug. 22, 2019 (9 pages).

"International Preliminary Report on Patentability," for PCT Application No. PCT/US2018/017944 dated Aug. 22, 2019 (7 pages).

"International Search Report and Written Opinion," for PCT Application No. PCT/US2017/069026 dated Apr. 3, 2018 (16 pages).

"International Search Report and Written Opinion," for PCT Application No. PCT/US2017/069035 dated Apr. 3, 2018 (16 pages).

"International Search Report and Written Opinion," for PCT Application No. PCT/US2018/017944 dated Apr. 26, 2018 (12 pages).

"International Search Report and Written Opinion," for PCT Application No. PCT/US2019/060296 dated Apr. 14, 2020 (14 pages).

"International Search Report and Written Opinion," for PCT Application No. PCT/US2019/060298 dated Apr. 28, 2020 (20 pages).

"International Search Report and Written Opinion," for PCT Application No. PCT/US2019/066358 dated Jun. 23, 2020 (18 pages).

(56) References Cited

OTHER PUBLICATIONS

"International Search Report and Written Opinion," for PCT Application No. PCT/US2019/068397 dated Apr. 14, 2020 (14 pages).
"Invitation to Pay Additional Fees and, Where Applicable, Protest Fee," for PCT Application No. PCT/US2019/066358 dated Mar. 5, 2020 (12 pages).
Klenk, et al., "Conceptualizing a Dynamic Fall Risk Model Including Intrinsic Risks and Exposures," JAMDA, 2017; 18:921-927 (7 pages).
Marschollek, et al., "Predicting In-Patient Falls in a Geriatric Clinic: a Clinical Study Combining Assessment Data and Simple Sensory Gait Measurements," Z Gerontol Geriatr, 2009; 42(4):317-321 (6 pages).
"Non Final Office Action," for U.S. Appl. No. 15/589,298 dated Jan. 2, 2019 (8 pages).
"Non Final Office Action," for U.S. Appl. No. 15/858,630 dated Sep. 4, 2018 (13 pages).
"Non-Final Office Action," for U.S. Appl. No. 15/589,298 dated Jul. 11, 2019 (13 pages).
"Non-Final Office Action," for U.S. Appl. No. 15/589,298 dated May 19, 2020 (15 pages).
"Non-Final Office Action," for U.S. Appl. No. 15/858,680 dated Jan. 16, 2020 (25 pages).
"Non-Final Office Action," for U.S. Appl. No. 15/895,311 dated Mar. 17, 2020 (26 pages).
"Notice of Allowance,"for U.S. Appl. No. 15/589,298 dated Jan. 22, 2020 (12 pages).
"Notice of Allowance,"for U.S. Appl. No. 15/858,630 dated Jul. 22, 2019 (10 pages).
"Notice of Allowance,"for U.S. Appl. No. 15/858,630 dated Nov. 1, 2019 (10 pages).
Oliver, "Falls Risk-Prediction Tools for Hospital Inpatients. Time to Put Them to Bed?," Age and Ageing, 2008; 37:248-250 (3 pages).
PathVU Mobile App, Pathway Accessibility Solutions, Inc., Pittsburgh, Pennsylvania [retrieved on Jun. 19, 2018. Retrieved from the Internet:<URL: http://www.pathvu.com/>; 6 pgs.
"Response to Final Office Action," for U.S. Appl. No. 15/858,630, filed with the USPTO dated Jun. 20, 2019 (11 pages).
"Response to Non Final Office Action," for U.S. Appl. No. 15/589,298, filed with the USPTO dated Apr. 1, 2019 (8 pages).
"Response to Non-Final Office Action," for U.S. Appl. No. 15/589,298, filed Aug. 19, 2020 (14 pages).
"Response to Non-Final Office Action," for U.S. Appl. No. 15/589,298 filed with the USPTO dated Oct. 3, 2019 (12 pages).
"Response to Non-Final Office Action," for U.S. Appl. No. 15/858,680, filed Apr. 16, 2020 (8 pages).
"Response to Non-Final Office Action," for U.S. Appl. No. 15/895,311, filed Jun. 12, 2020 (10 pages).
"Resposne to Non Final Office Action," for U.S. Appl. No. 15/858,630 filed with the USPTO dated Dec. 3, 2018 (11 pages).
Rumalla, et al., "The Effect of Hearing Aids on Postural Stability," Laryngoscope, 2015; 125(3):720-723 (4 pages).
Salisbury, Joseph P. et al., "Patient Engagement Platform for Remote Monitoring of Vestibular Rehabilitation with Applications in Concussion Management and Elderly Fall Prevention," 2018 IEEE International Conference on Healthcare Informatics, pp. 422-423.
Viikki, "Machine Learning on Otoneurological Data: Decision Trees for Vertigo Diseases," Academic Dissertation, University of Tampere, Finland, 2002; 84 pages.
Yang, et al., "Fall Risk Assessment and Early-Warning for Toddler Behaviors at Home," Sensors, 2013; 13:16985-17005 (21 pages).
"Communication Pursuant to Article 94(3) EPC," for European Patent Application No. 17838110.9 dated Feb. 1, 2022 (8 pages).
"European Search Report," for European Patent Application No. 19212657.1 dated Feb. 14, 2020 (10 pages).
"Final Office Action," for U.S. Appl. No. 15/858,680 dated May 10, 2021 (23 pages).
"Final Office Action," for U.S. Appl. No. 15/895,311 dated Apr. 13, 2021 (9 pages).
"International Preliminary Report on Patentability," for PCT Application No. PCT/US2019/066358 dated Jun. 24, 2021 (12 pages).
"International Preliminary Report on Patentability," for PCT Application No. PCT/US2019/068397 dated Jul. 8, 2021 (9 pages).
"International Preliminary Report on Patentability," for PCT Application No. PCT/US2020/026435 dated Oct. 14, 2021 (8 pages).
"International Search Report and Written Opinion," for PCT Application No. PCT/US2020/026435 dated Jul. 9, 2020 (12 pages).
"Non-Final Office Action," for U.S. Appl. No. 15/858,680 dated Dec. 22, 2020 (22 pages).
"Non-Final Office Action," for U.S. Appl. No. 15/895,311 dated Feb. 23, 2021 (12 pages).
"Non-Final Office Action," for U.S. Appl. No. 16/714,339 dated May 17, 2021 (34 pages).
"Notice of Allowance," for U.S. Appl. No. 16/714,339 dated Nov. 2, 2021 (13 pages).
"Response to Final Office Action," for U.S. Appl. No. 15/858,680, filed Oct. 8, 2021 (9 pages).
"Response to Final Office Action," for U.S. Appl. No. 15/858,680, filed Oct. 21, 2020 (11 pages).
"Response to Final Office Action," for U.S. Appl. No. 15/895,311, filed Oct. 19, 2020 (13 pages).
"Response to Final Office Action," for U.S. Appl. No. 15/895,311, filed Sep. 13, 2021 (7 pages).
"Response to Non-Final Office Action," for U.S. Appl. No. 15/858,680, filed Mar. 22, 2021 (15 pages).
"Response to Non-Final Office Action," for U.S. Appl. No. 15/895,311, filed Mar. 17, 2021 (7 pages).
"Response to Non-Final Office Action," for U.S. Appl. No. 16/714,339, filed Sep. 15, 2021 (6 pages).
Leake, Jason Llewellyn "Fall Detectors for People with Dementia," University of Bath Student Thesis, Jun. 2016 (364 pages).
Zheng, et al. "Effect of postural changes on lower limb blood volume, detected with non-invasive photoplethysmography," Journal of Medical Engineering & Technology, vol. 32, No. 5, Sep./Oct. 2008, pp. 358-364 (7 pages).
"International Search Report and Written Opinion," for PCT Application No. PCT/US2021/057064 dated Feb. 10, 2022 (15 pages).
"Non-Final Office Action," for U.S. Appl. No. 15/858,680 dated Apr. 8, 2022 (22 pages).
"Non-Final Office Action," for U.S. Appl. No. 15/895,311 dated Feb. 9, 2022 (17 pages).
"Final Office Action," for U.S. Appl. No. 15/858,680 dated Aug. 12, 2022 (19 pages).
"Final Office Action," for U.S. Appl. No. 15/895,311 dated Jul. 18, 2022 (15 pages).
"Response to Non-Final Office Action," for U.S. Appl. No. 15/858,680, filed Jul. 8, 2022 (10 pages).
"Response to Non-Final Office Action," for U.S. Appl. No. 15/895,311, filed Jun. 9, 2022 (9 pages).
Wen, Jiaqu, et al. "We Help You Watch Your Steps: Unobtrusive Alertness System for Pedestrian Mobile Phone Users," 2015, IEEE International Conference on Pervasive Computing and Communications (PerCom), pp. 105-113 (9 pages).
"Non-Final Office Action," for U.S. Appl. No. 15/858,680 dated Jan. 25, 2023 (23 pages).
"Non-Final Office Action," for U.S. Appl. No. 15/895,311 dated Dec. 28, 2022 (21 pages).
"Response to Non-Final Office Action," for U.S. Appl. No. 15/895,311, filed Mar. 20, 2023 (15 pages).

* cited by examiner

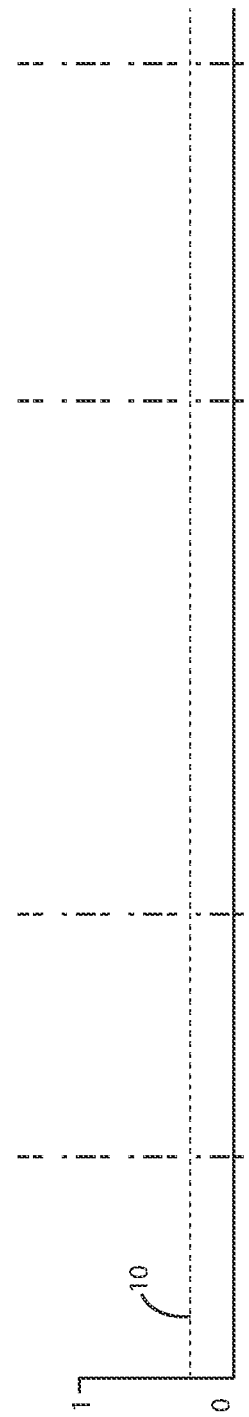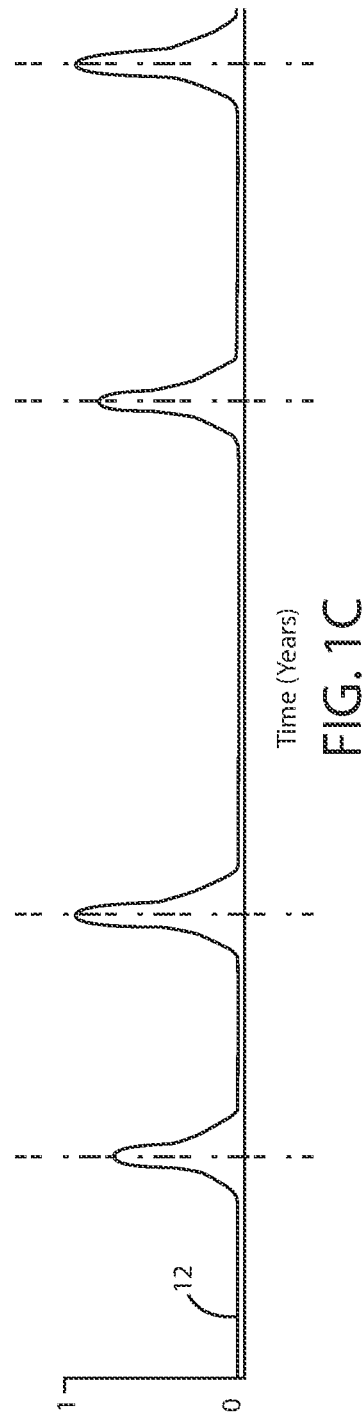

PREDICTIVE FALL EVENT MANAGEMENT SYSTEM AND METHOD OF USING SAME

This application claims the benefit of U.S. Provisional Application No. 62/785,295, filed Dec. 27, 2018, the content of which is herein incorporated by reference in its entirety.

FIELD

Aspects herein relate to predictive fall event management systems and related methods.

BACKGROUND

Maintaining postural control and preventing a fall are of importance for the elderly. Falls are the second leading cause of accidental or unintentional injury deaths worldwide and are especially prevalent in the elderly. Currently, individuals are often inadequately prepared to protect themselves from falls or other serious injuries as the onset of such events can come without perceptible warning. Further, maintaining postural equilibrium, i.e., prevention of a fall, involves stabilization of the body's center of mass during both self-initiated and externally triggered disturbances to postural stability during normal daily activities. Maintaining such equilibrium can be accomplished by limiting the motion of the center of mass within the base of support formed by and around the feet. Postural equilibrium is maintained through multisensory inputs. For example, loss of sensory input in the feet due to neuropathy can increase the risk of a fall, even though the necessary motor control for a corrective action of repositioning the feet can still be intact. Similarly, low vision or reduced ranges of hearing can prevent an individual from detecting hazards within their environment such that they can avoid them.

SUMMARY

In general, the present disclosure provides various embodiments of a predictive fall event management system and a method of utilizing such system. In various embodiments, the system evaluates future risk conditions that can be used to predict the occurrence of fall events. In one or more embodiments, the system can include a body-worn device and a controller operatively connected to the body-worn device. The controller can be adapted to determine, for a future time, whether a fall condition is satisfied based upon one or more future physiological states or contextual states of a wearer of the body-worn device. Such future physiological states and contextual states can be determined based upon one or more physiological data and contextual data related to the wearer.

In one aspect, the present disclosure provides a predictive fall event management system that includes a body-worn device and a controller operatively connected to the body-worn device. The controller is adapted to receive physiological data representative of a physiological characteristic of a wearer of the body-worn device over a monitoring time period, receive contextual data representative of context information of the wearer over the monitoring time period, and determine one or more future physiological states or contextual states based at least in part on one or more of the physiological data and the contextual data. The controller is further adapted to determine, for a future time, whether a fall condition is satisfied based upon the one or more future physiological states or contextual states and generate a fall prevention output responsive to satisfaction of the fall condition.

In another aspect, the present disclosure provides a method that includes receiving physiological data representative of a physiological characteristic of a wearer of a body-worn device over a monitoring time period, receiving contextual data representative of context information of the wearer over the monitoring time period, and determining one or more future physiological states or contextual states based at least in part on one or more of the physiological data or the contextual data. The method further includes determining, for a future time, whether a fall condition is satisfied based upon one of the one or more future physiological states or contextual states and generating a fall prevention output responsive to satisfaction of the fall condition.

These and other aspects of the present disclosure will be apparent from the detailed description below. In no event, however, should the above summaries be construed as limitations on the claimed subject matter, which subject matter is defined solely by the attached claims, as can be amended during prosecution.

BRIEF DESCRIPTION OF THE DRAWINGS

Throughout the specification, reference is made to the appended drawings, where like reference numerals designate like elements, and wherein:

FIG. 1A is a graph of frequency of a fall versus time for an individual.

FIG. 1B is a graph of standard predicted probability of a fall versus time for the individual of FIG. 1A.

FIG. 1C is a graph of predicted probability of a fall versus time for the individual of FIG. 1A.

FIGS. 2A-C are graphs of weighted risk factors for a fall versus time, wherein FIG. 2A is a graph of balance risk factors based upon a screening test versus time for an individual, FIG. 2B is a graph of a medication's risk factors versus time for the individual, and FIG. 2C is a graph of risk factors associated with the individual moving from a seated to a standing position versus time.

FIG. 3A is a graph of an overall risk of a fall versus time for the individual one hour after the individual ingests a particular medication, and FIG. 3B is a graph of the overall risk of a fall versus time for the individual seven hours after ingestion of the medication.

DETAILED DESCRIPTION

Figure 2A:
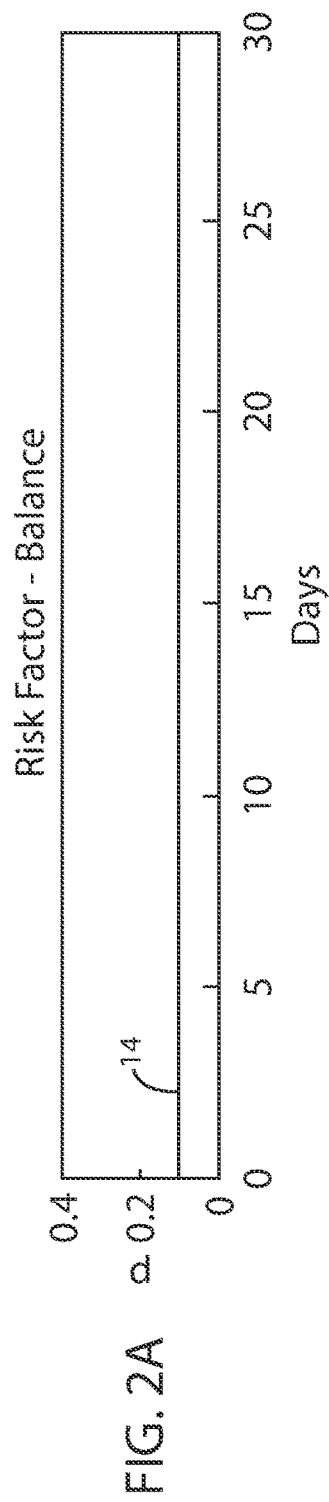

In general, the present disclosure provides various embodiments of a predictive fall event management system and a method of utilizing such system. The system can include a body-worn device and a controller operatively connected to the body-worn device. The controller can be adapted to determine, for a future time, whether a fall condition is satisfied based upon one or more future physiological states or contextual states of a wearer of the body-worn device. Such future physiological states and contextual states can be determined based upon one or more physiological data and contextual data related to the wearer.

Real-world fall risk factors that can lead to a fall by an individual can be dynamic and not constant as they can change over time and are highly individualized. Current methods of assessing the individual's risk for falling do not account for these complex, real-world dynamics. Presently, clinical techniques for assessing an individual's long-term falls risk level are performed in a hospital or doctor's office. Generally, these tests are not assessed frequently enough to track abrupt changes in risk level, such as when an individual has changed her medications. Moreover, these clinical tests may not be sensitive enough to monitor gradual declines and improvements that might occur moment to moment. Other techniques that can be utilized remote from a clinical setting can detect the onset and early stages of falls, in some cases prior to the individual impacting the ground.

A near-term prediction system that can account for both an individual's long-term risk level and momentary risk level is desirable. This type of predictive fall event management system would inform a user of momentarily-elevated risks levels or take automated actions, on the user's behalf, to reduce her risk of falling during her daily activity. Customized interventions for near-term risk factor mitigation can also be informed by knowledge of the user's long-term risk factors.

One or more embodiments of the present disclosure provides a predictive fall event management system that can utilize time-varying physiological and contextual factors. Instead of only weighing a user's various risk factors, the system can adapt to physiological and contextual information related to the user and employ individualized learning that can modify the system over time. In one or more embodiments, the system can apply different weights to the various fall risk factors depending upon their influence on one or more fall risk levels and the recency and certainty of available contextual information such as the user's environment, schedule, medical history, etc. Over varying periods of time, values or statistics representing fall risk factors can either be extinguished or maximized by the system, unless these risk factor estimations continue to be supported by more recent data. In one or more embodiments, the recency of input data can affect the statistics, e.g., the confidence intervals relative to the risk factors assessed using the input data. Risk factor weightings can also have condition-specific dependencies that can influence the extinction and maximization of the fall risk level estimations. Similarly, the strength or severity of condition-specific dependencies and associations can affect the statistics, e.g., the confidence intervals relative to the risk factors assessed using the input data.

In currently-available fall risk systems, long-term risk factors can be assessed, but long-term risks can only be mitigated with indirect, general fall prevention strategies like physical therapy, occupational therapy, medication review, counseling, home environment modification, etc. In one or more embodiments, a near-term fall prediction can anticipate a fall prior to the individual losing her balance, from which she may not be able to recover without falling. A near-term falls prediction system can be useful for accurately informing a user of momentarily elevated risks levels and taking automated actions on the user's behalf during daily activity.

Given the multiplicity of causes for falls, the taxonomy of fall risk can be broken down into many risk factors. Some factors can affect the user for a long period of time (i.e., long-term risk factors such as age-related balance system deterioration), while others may affect the user over a relatively short period of time (i.e., short-term risk factors such as a decrease of oxygen level in the brain due to sudden movement). At any given time, a risk factor may or may not impose real fall risks because the factor also depends on the conditions (i.e., states or contexts) that the user may be experiencing.

Consider when an individual, who is associated with a high falls risk level due to a muscle weakness, sits in a chair. At that moment, the individual can have a low risk of falling; however, once the individual initiates a postural transition (e.g., attempts to stand), the individual can be more at-risk for falling within the time period immediately following the individual initiating the change in posture. If the individual moves properly, the individual may not fall, but if the individual shifts her weight incorrectly, she may begin to lose postural control and fall. Often, individuals with lower limb muscle weakness struggle to stand from a seated position and may need to make several attempts. In these few seconds, the individual's intent and stability can be analyzed, and guidance could be provided to the user to prevent a fall from occurring.

In another example, an individual can have an elevated risk level of a fall due to balance problems resulting from a knee injury. This individual's primary falls risk factor does not put the individual at real risk for falling while the individual is stationary (e.g. standing, sitting or lying), but the risk level can increase once the individual starts to walk. The risk of falling may be further increased if the individual increases the walking speed and/or walks on a slippery surface.

There are numerous falls risk factors that can be measured or inferred for a user. In general, falls risk factors can be characterized as intrinsic or extrinsic. Risk factors for falling, however, rarely remain constant over time. In addition, the contributions of falls risk factors to the real risk of a fall also depend on the states, contexts and conditions that a patient is in (e.g., postural position, activity, environment, alertness, etc.). Fall risks have traditionally only been assessed in terms of a general, long-term fall risk level. Other systems, namely those that include airbags that are intended to reduce the physical impact of a fall on an elderly person's hips, have been able to detect the onset of falls prior to the individual reaching the ground. These predictions are made, however, within roughly 200 milliseconds of the individual hitting the ground. Within this extremely short time period, not much can be done to prevent the inevitable fall from occurring. A near-term assessment of momentary falls risk can enable taking actionable steps to reduce the individual's risk for falling at a future time.

The frequency of actual falls versus both the state-of-the-art and one or more embodiments of fall event management systems described herein can be contrasted graphically as shown in FIGS. 1A-C. As shown in FIG. 1A, an individual experiences actual falls at times $t_1$, $t_2$, $t_3$, and $t_4$. Although the actual falls are discrete events, a current risk prediction model, which is illustrated by curve 10 of FIG. 1B, provide a constant probability of a fall over a period of time (i.e., a monitoring time period). One or more embodiments of a predictive fall event management systems of the present disclosure can provide a system that incorporates time-dependent and time-independent fall risk factors using techniques that can be time dependent or independent as schematically illustrated by curve 12 of FIG. 1C.

Further, the present disclosure can provide one or more embodiments of a predictive fall event management system that utilizes time-varying risk and context factors. Instead of weighing an individual's different risk factors, one or more embodiments of a system described herein, that can adapt to physiological and contextual information related to a user and utilize individualized learning, can provide one or more predictions of the potential that the user may fall at a given point in the future. Conceptually, the system applies different weights to the various fall risk factors depending upon their influence on a falls risk level and the recency and certainty of the available contextual information. After varying lengths of time, either the values or statistics or the contributions of various risk factors may be extinguished or maximized in a particular user's fall event management system.

For example, a fall event, in a unit time interval (UTI), can be modeled by a Bernoulli random variable, given that the unit interval is short enough such that the chance of falling twice can be neglected. The length of the UTI depends on the time taken for an individual to recover to an upright posture after a fall event, assuming no significant consequences to the user were caused by the fall such as a broken limb or unconsciousness. The value of UTI can vary from a few seconds to a few minutes. Some people may need longer recovery time than others (e.g. elderly individuals may take a longer time to stand up after falling down than young healthy individuals) or, indeed, some individuals may actually be at risk for falling again as they attempt to stand up after a fall and require a shorter UTI. In fact, because falls are a relatively rare event, for many individuals, the UTI can sometimes be extended to hours, days, or even weeks or months, until the occurrence of certain events such as a fall or when time-sensitive risk factors occur.

In general, one or more embodiments of predictive fall event management systems described herein can estimate a probability of a fall (the value in the Bernoulli distribution) for each future unit time interval, $t_n$, $$\hat{p}(t_n) = M(r_1, r_2, r_3, \ldots | c_1, c_2, c_3, \ldots)$$

where $r_i$ and $c_j$ represent the different risk factors and conditions, respectively, whose values can also be time varying, i.e., $r=r_i(t)$ and $c_j=c_j(t)$, and can be modeled by risk factor models and condition models.

On the one hand, some risk factors are independent from or are weakly correlated to others, based on which the probabilities of falls can be estimated independently. On the other hand, many other risk factors can be highly dependent upon each other, and the fall risks can be estimated jointly. These relationships can be determined, and the disclosed fall risk model can be written as the sum of many sub-models:

$$\hat{p}(t_n) \approx M_1(r_1 | c_1, c_2, c_3, \ldots) + M_2(r_2 | c_1, c_2, c_3, \ldots) + \ldots + M_i(r_{i\_1}, r_{i\_2} \ldots | c_1, c_2, c_3, \ldots)$$

As an illustration, orthostatic hypotension can be a binary risk factor based on a medical history screening (i.e., yes or no), or it can be a measured risk factor (i.e., an observed decrease in blood pressure after standing up). In either case, these two inputs would not offer substantially different information from each other, so for some embodiments their weightings in the predictive fall event management system can be collapsed into a singular weighting or as individual factors with an otherwise reduced weighting when factored separately. That said, the measured variant can make the risk factor more time- or context-specific, and thus more predictive and deserving of a higher weighting value than that of the binary risk factor that could have been reported days, weeks, months, or even years earlier. Likewise, the medical history risk factor can serve to validate a measured risk factor, and the applied weighting can be adapted since it is somewhat based upon a clinical observation. Similarly, measures of physical strength, like handheld myometry, might overlap with other forms of physical strength measurement such as the sit-to-stand test or TUG test or the like. Characteristics of these clinical tests can also be measured during ambulatory activities, but similar elements contributing to the risk estimation, stemming from a variety of inputs, can be prevented from biasing the predictive fall event management system by identifying or assigning duplicated factor values or statistics in the equation of a sub-model. As such, a complex and adaptive risk factors classification and weightings database can be maintained for the system to reference.

One or more sub-models of the predictive fall event management system can be derived based on known principles and/or trained based on learned data. Depending upon the nature of the risk factors, various machine learning models can be applied to generate the sub-models (e.g., linear regression, decision tree, Bayesian models, neural network, Kalman filtering, etc.). The confidence intervals of a prediction by each sub-model can also be computed and compared to an overall confidence interval for the overall prediction of the system.

One or more embodiments of the disclosed predictive fall event management system can predict the probability of falling at a future time (i.e., a fall condition) beyond the immediate UTI, i.e., over a monitoring time period, which can be enabled by incorporating the time varying risk factor values and conditions $r_i$ and $c_j$. As used herein, the term "fall condition" refers to a condition where a wearer of the body-worn device is at risk for experiencing a fall, e.g., where a probability of a fall crosses a threshold, or a model indicates that a fall has occurred or can occur in a state having similarities to a predicted state. In one or more embodiments, a fall condition can also be or include a predicted or potential outcome of a fall, e.g., a likelihood of injury or a magnitude of an injury. It will be appreciated that the "probability of a fall" can include various other statistical metrics, such as a confidence interval or value related to the calculated "probability of a fall."

Figure 2B:
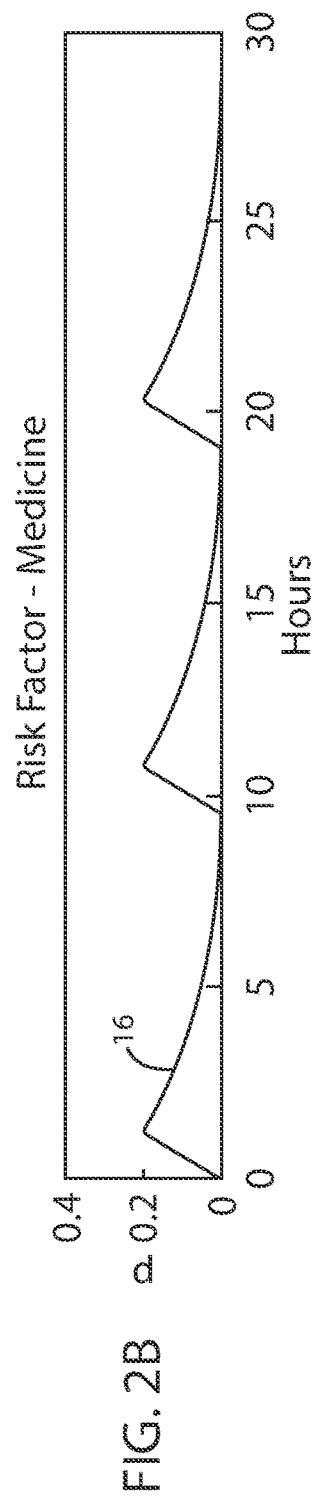
Figure 2C:
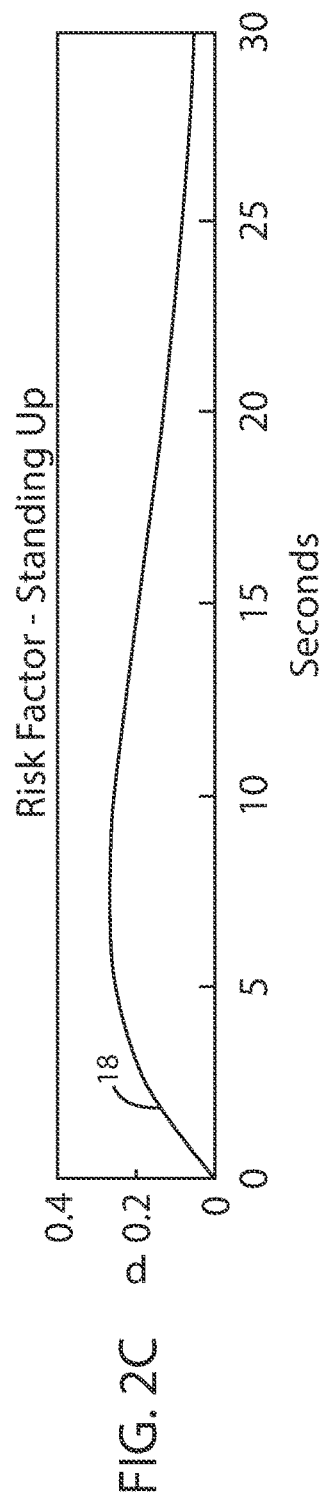

FIGS. 2A-C are graphs of weighted fall risk values or factors versus time for a user that ingests a medication that causes dizziness. In this illustrative example, such dizziness often peaks at thirty minutes after ingestion and then dissipates over a period of, e.g., about four hours as is illustrated by curve 16 of FIG. 2B. The system can also evaluate other fall risk values or factors such as the particular user's historical balance risk value as shown by curve 14 in FIG. 2A and the user's historical balance data for when the user stands up from a seated position as illustrated by curve 18 in FIG. 2C.

Figure 3A:
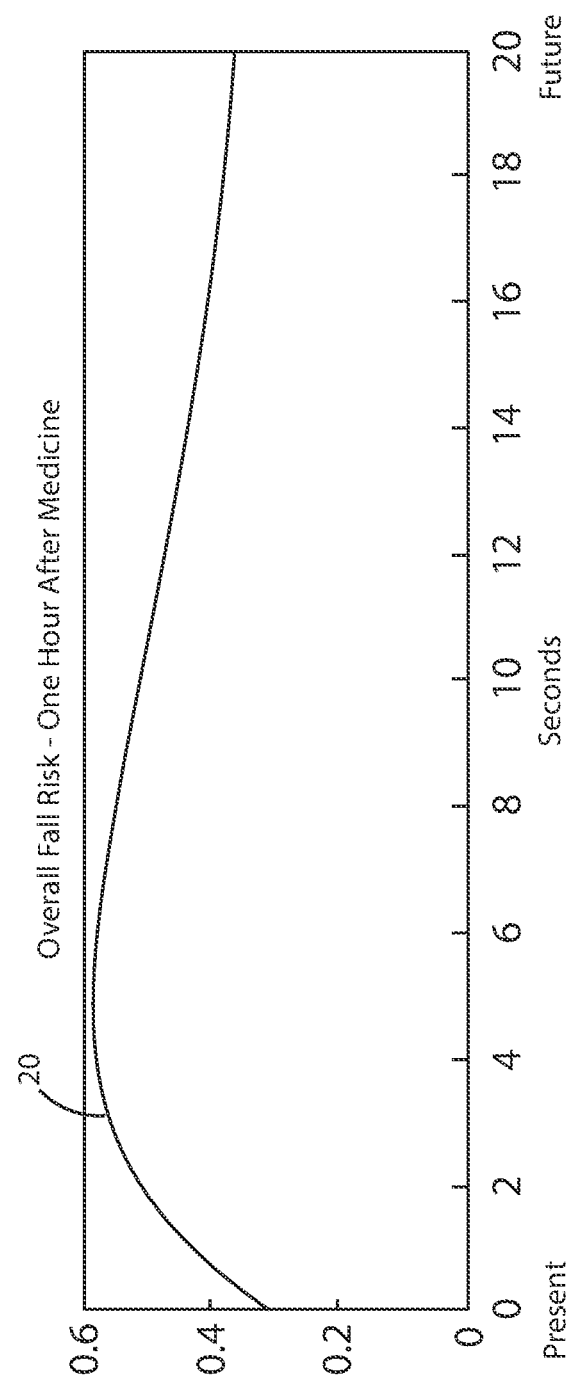
FIGS. 3A-B are graphs of weighted overall risk factors of a fall for the individual of FIGS. 2A-C, where
Figure 3B:
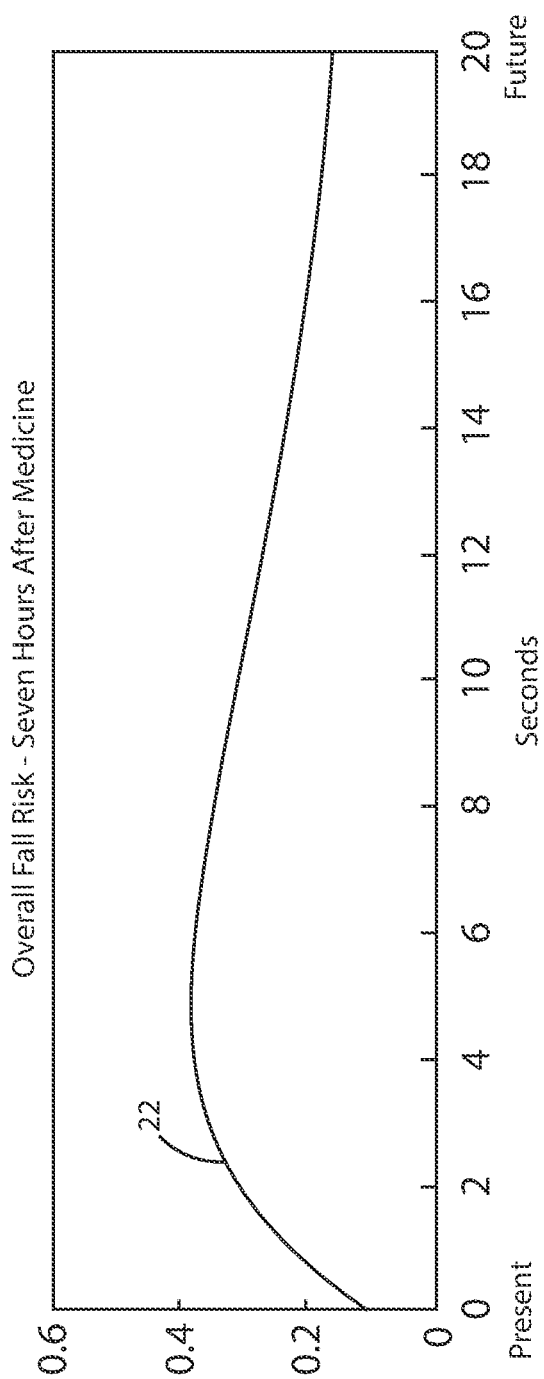

As a result of building this knowledge into the predictive fall event management system, at the time of ingesting the medication, the output of the system can predict whether a fall condition is satisfied around the time that dizziness or blurred vision is projected to peak as shown by curve 20 of FIG. 3A, which is the weighted composite fall risk value for the user one hour after ingestion of the medication, and curve 22 of FIG. 3B, which is the weighted composite fall risk value seven hours after ingestion of the medication. The level of dizziness can be updated using, e.g., Kalman filtering approaches, in real time, if informative physiological information can be measured or if relevant questionnaires can be administered. Thus, the fall risk can be recomputed as new information is added. If the medicine is taken periodically, then the historical data relating to dizziness level or imbalance, associated with previous occurrences of taking the medicine, can be used to customize the medicine's effects on the user, thereby improving the accuracy of the individual's fall risk estimation. In further embodiments, historical data relating to dizziness level or imbalance, associated with previous occurrences of taking the medicine, can be used to assist the user or a medical professional in optimizing the times at which the user takes their medications such that the user's risk for falling would be minimized when the user is predicted to be ambulatory or otherwise exposed to conditions or contexts that would elevate the individual's risk for falling.

As a second example, based on calendar information and/or activity logging history of the user, one or more embodiments of the predictive fall event management system can infer that the user will be walking to an appointment within the next hour. At the same time, the sidewalks on which the user will be traversing to get to the appointment have been reported, by other users, weather predictions, or hazard beacons, to be slippery due to icy conditions. As a result, these sidewalks can be assigned a high value as an extrinsic falls risk factor for users until four hours later when the temperature is expected to become sufficiently warm, long enough to melt the ice. Based on these physiological and contextual factor predictions, the related fall risk sub-model can predict a sharp increase of a fall risk in one hour. Depending on whether the user has other high-value risk factors, the overall fall risk predicted by the system can satisfy a fall condition, thereby triggering one or more fall prevention outputs such as warnings well ahead of the predicted fall so that the user can react accordingly. In this example, the user can optionally be prompted with the risk estimate and then asked about their planned method of travel. The user can be directed to call for a driver or to contact a caregiver to assist them in making it to the appointment safely. In one or more embodiments, these tasks can be initiated or otherwise undertaken upon the user's behalf by an electronic system or an artificial intelligence assistant.

As mentioned in these examples, the physiological factor models and contextual factor models can be adapted to each individual user, over time, by comparing the model prediction and any present observations that are available. These adaptations can also be informed by data collected from individuals or groups of individuals other than the user. Classification and weighting of each risk factor, which can be stored in one or more databases, can assist in assigning values to the risk factor based upon the severity of the condition (i.e., risk factor scaling), its known predictive value, statistics, (e.g., confidence intervals), recency of the input data, and the novelty of information that each input provides into the user's falls risk determination. These databases can also have values or statistics and offsets that account for the fact that not every possible input available for calculation into the predictive fall event management system will have been measured or entered into the system for that individual. This may change over time as more information is collected (or expires) regarding the individual user, so the database can provide dynamic values or statistics based upon which inputs are being factored into any given user's risk estimation at any given time. Changes in risk factor weightings over time can also be stored as "time coefficients" within the risk factors classification and weightings database.

Conditions or thresholds can be set for individual composite risk estimation values, the corresponding time in the future, and their respective statistics, e.g., the size of the confidence intervals. These conditions may be stepped in any appropriate manner to indicate degrees of severity (e.g., high, medium, low), and different actions and interventions may be triggered at different condition levels. Further, data trends can be stored and reviewed for comparison over time. A count of how frequently conditions are satisfied can also be maintained in memory. These data may be accessed by the user or other interested parties and for machine learning that can be adapted to modify the predictive fall event management system. As mentioned in the previous icy street example, the user might be warned before encountering the icy street such that the user can, e.g., change routes, alter their means of travel, or reschedule the appointment. Further, the types of actions and interventions from the system can vary for different situations. In the earlier example of the patient having a muscle weakness, if the user struggles to stand on her own after standing up (e.g., her walker is not positioned properly), the system can be adapted to generate a fall prevention output such as instructing the user to wait for assistance and informing other individuals who may be able to provide that assistance to the user. Similarly, if the user stands but orthostatic hypotension is detected, then the system can be adapted to generate a fall prevention output that informs the user that she may feel lightheaded or dizzy and instructs her to wait a few moments before beginning to walk. In one or more embodiments, the fall prevention output may be directed at controlling an operatively connected assistive device or exoskeleton.

Figure 4:
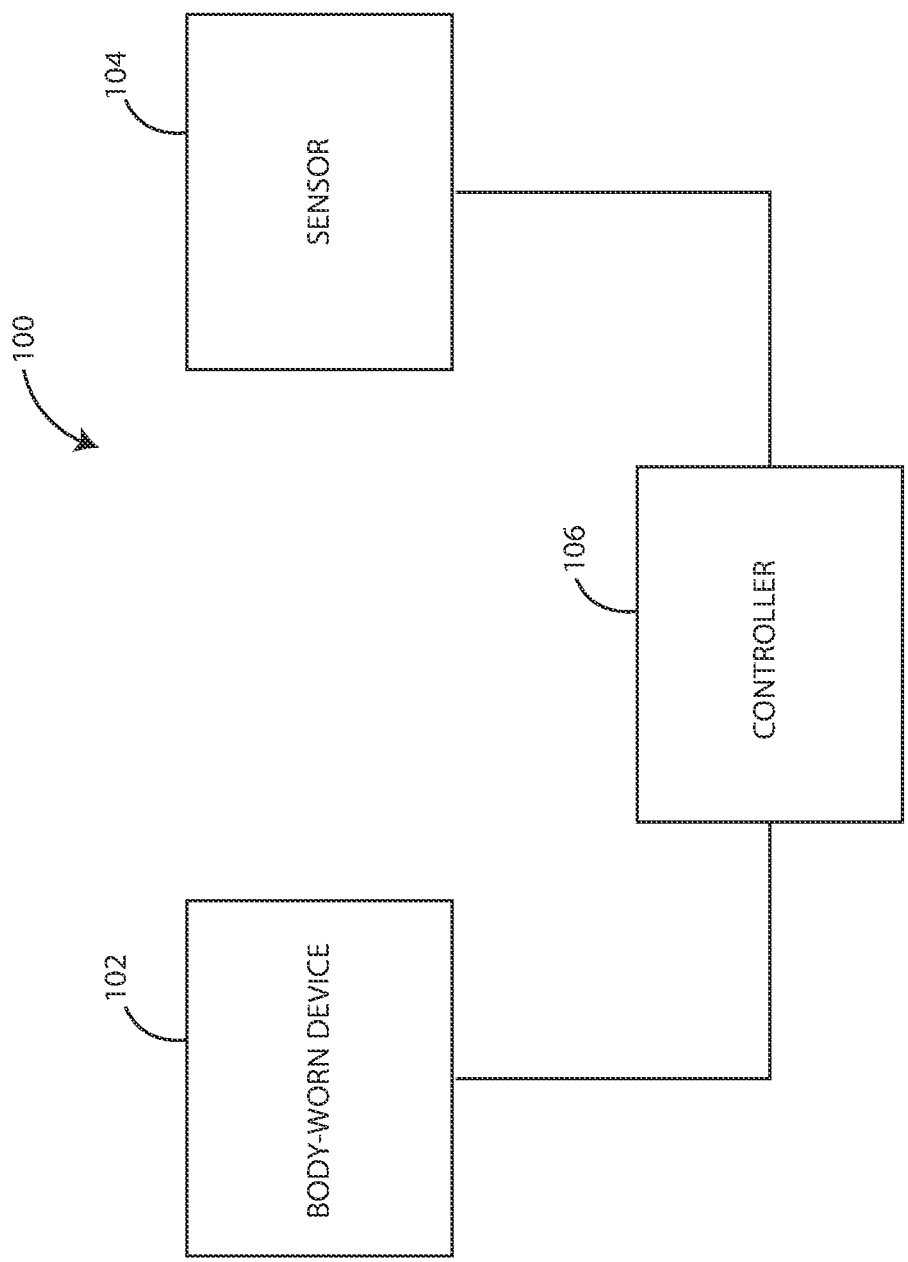
FIG. 4 is a schematic diagram of one embodiment of a predictive fall event management system.

Any suitable fall prediction system or device can be utilized for fall prediction, prevention, and/or detection. For example, FIG. 4 is a schematic diagram of one embodiment of a predictive fall event management system 100. The system 100 includes a body-worn device 102 for a wearer, an optional sensor 104 operatively connected to the body-worn device, and a controller 106 operatively connected to one or both of the body-worn device and the controller. As used herein, the term "operatively connected" means that an element or component can be connected to another element or component using any suitable technique or techniques such that information can be shared between such components. In one or more embodiments, the sensor 104 can be operatively connected to the body-worn device 102 by a wire or cable, wirelessly using any suitable wireless protocol, optically, over the internet, mesh network, etc.

In one or more embodiments, the controller 106 is adapted to receive physiological data representative of a physiological characteristic of a wearer of the body-worn device over a monitoring time period, receive contextual data representative of context information of the wearer over the monitoring time period, and determine one or more future physiological states or contextual states based at least in part on one or more of the physiological data and the contextual data. As used herein, the term "physiological data" refers information regarding the wearer's physiological state, e.g., at least one of a determined fall risk, inertial sensor data, heart rate information, blood pressure information, drug concentration information, blood sugar level, body hydration information, neuropathy information, blood oximetry information, hematocrit information, cortisol level, body temperature, age, sex, gait or postural stability attribute, vision, hearing, eye movement, neurological activity, head movement, or the like. In one or more embodiments, physiological data can include psychological data representative of a psychological state such as a fear of falling. Such psychological state can, in one or more embodiments, be detected from physiological data or combinations of physiological data such as heart rate, core body temperature, or cortisol levels. Further, in one or more embodiments, the physiological data can include, in part or in combination, one or more inputs provided by the wearer in response to one or more queries.

Further, as used herein, the term "contextual data" refers to data representative of a context within which the user is disposed or will be disposed at a future time. In one or more embodiments, contextual data can include at least one of weather condition, environmental condition, sensed condition, location, velocity, acceleration, direction, hazard beacon, type of establishment occupied by the wearer, camera information, or presence of stairs, etc. One or more hazard beacons can provide contextual data to the system 100. Such hazard beacons can include physical or virtual beacons as described, e.g., in U.S. Patent Publication No. 2018/0233018 A1, entitled FALL PREDICTION SYSTEM INCLUDING A BEACON AND METHOD OF USING SAME.

As used herein, the term "future physiological state" means values or statistics relative to a physiological state that is predicted to occur at a future time, where such statistics can include one or more of a probability, confidence interval, distribution, range, or the like. Further, as is also used herein, the term "future contextual state" means values or statistics relative to a contextual state that is predicted to occur at a future time, where such statistics can include one or more of a probability, confidence interval, distribution, range, or the like.

The future time of the contextual data and/or future physiological state can vary. In some embodiments, the future time can be about 5 seconds, 10 seconds, 30 seconds, 60 seconds, 2 minutes, 5 minutes, 10 minutes, 20 minutes, 30 minutes, 45 minutes, 60 minutes, 90 minutes, 120 minutes, 180 minutes, 240 minutes, 300 minutes, 12 hours, 24 hours, 48 hours, 72 hours, 1 week or longer, or an amount of time falling within a range between any of the foregoing.

The controller 106 is also adapted to determine, for a future time, whether a fall condition is satisfied based upon the one or more future physiological states or contextual states and generate a fall prevention output responsive to satisfaction of the fall condition. As used herein, the term "fall condition" refers to a condition where a wearer of the body-worn device is at risk for experiencing a fall, e.g., where a probability of a fall crosses a threshold, or a model indicates that a fall, near-fall, or balance event has occurred or may occur in a state having similarities to a predicted state. In one or more embodiments, a fall condition may also be or include a predicted or potential outcome of a fall, e.g., a likelihood of injury or a predicted magnitude of an injury.

The future time for determination of whether a fall condition is satisfied can vary. In some embodiments, the future time can be about 5 seconds, 10 seconds, 30 seconds, 60 seconds, 2 minutes, 5 minutes, 10 minutes, 20 minutes, 30 minutes, 45 minutes, 60 minutes, 90 minutes, 120 minutes, 180 minutes, 240 minutes, 300 minutes, 12 hours, 24 hours, 48 hours, 72 hours, 1 week or longer, or an amount of time falling within a range between any of the foregoing.

Any suitable technique or techniques can be utilized by the controller 106 to determine whether a fall condition is satisfied. For example, in one or more embodiments, the controller 106 can be further adapted to determine, for a future time, whether the fall condition is satisfied by determining a future fall risk value based upon the one or more future physiological states or contextual states. As used herein, the term "future fall risk value" means value or statistics relative to a fall risk value that is predicted to occur at a future time, where such statistics can include one or more of a probability, confidence interval, distribution, range, or the like. The controller 106 can further be adapted to receive balance data representative of a balance event and update the fall risk model based upon one or more of the physiological data, contextual data, and the balance data.

In one or more embodiments, the controller 106 can be adapted generate a fall prevention output responsive to satisfaction of the fall condition. Any suitable fall prevention output can be provided that can assist in mitigating the risk of the user falling, e.g., one or more of an audible alert, visual alert, or tactile alert provided to the wearer. For example, the user can be warned of the user acting on a predicted behavior when the predicted risk associated with the predicted behavior crosses a threshold for alerting the user. Thresholds for alerting the user and/or undertaking other fall prevention outputs can vary. In some embodiments, the thresholds can be specified in terms of a probability of a fall occurring and can be about 10, 20, 30, 40, 50, 60, 70, 80, 90, 95, 98, or 99 percent, or an amount falling within a range between any of the foregoing. In some embodiments, the specific fall prevention output undertaken can vary based on the probability of the fall occurring, with more aggressive fall prevention outputs being taken when the probability of a fall occurring is higher. The thresholds can be preset when the system is manufactured, can be set/reset if the system determines that the user's (device wearer's) long-term risk for falling has changed, can be set by a care provider or clinician, can be set by the device wearer, or the like. In some cases the thresholds can be static and in other cases the thresholds can be dynamic.

In one or more embodiments, the user can be advised of suitable options or alternatives to acting on a particular predicted behavior to protect the user from engaging in unnecessary risky behaviors. In one or more embodiments, the user can be given directions or advice to mitigate their risks. In one or more embodiments, the use of virtual reality or augmented reality such as those described, e.g., in U.S. Patent Publication No. 2018/0233018A1, entitled FALL PREDICTION SYSTEM INCLUDING A BEACON AND METHOD OF USING SAME can be used to assist the user in avoiding potential risks.

In some embodiments, the fall prevention output can include electrical stimulation and/or thermal stimulation. Aspects of stimulation and other outputs are described in U.S. Pat. Appl. No. 62/873,598 entitled "SYSTEMS AND DEVICES FOR TREATING EQUILIBRIUM DISORDERS AND IMPROVING GAIT AND BALANCE", the content of which is herein incorporated by reference.

In one or more embodiments, the fall prevention output can include initiating a mitigation therapy or corrective measures e.g., a balance training regimen. The fall prevention output can further include controlling or modifying one or more features and actions of a mobility device, an assistive device, or an exoskeleton.

In one or more embodiments, the fall prevention output can include one or more modifications of an environmental context of the wearer. Any suitable environmental contexts can be modified to satisfaction of a predicted fall condition. For example, the fall prevention output can include modifying, via mesh networks or the internet of things (IoT), e.g., the lighting within an area proximate to the user or within an area where the user is predicted to be.

Similarly, the fall prevention output can include modifying the temperature, oxygen mix, humidity, or air quality of an area proximate to the user or within an area where the user is predicted to be. Further, in one or more embodiments, the fall prevention output can include transmission of one or more of the physiological data and the contextual data to one or more of a caregiver, a medical professional, a database, or the wearer.

In one or more embodiments, the fall prevention output can also include adapting one or more of a fall detection system setting such that the fall detection system is more likely to indicate that a fall has occurred if the predicted fall risk statistics crossed a certain threshold leading up to the occurrence in question as described, e.g., as described in U.S. patent application Ser. No. 16/714,339, entitled "HEARING ASSISTANCE SYSTEM WITH ENHANCED FALL DETECTION FEATURES". In one or more embodiments, the adaption of fall detection system settings can be applied transitorily such that the system is only more likely to indicate that a fall has occurred for a period of seconds or minutes. In one or more embodiments, the adaption of fall detection system settings can be applied over a longer period of time.

Further, in one or more embodiments, the controller 106 can be further adapted to determine, for each of a plurality of future times, whether an anticipated fall condition is satisfied based upon one or more of the physiological data and the contextual data. Further, in one or more embodiments, the controller 106 can further be adapted to determine, for a plurality of future times, whether an anticipated fall condition is satisfied based upon a combination of the physiological data and the contextual data.

The controller 106 can further be adapted to detect disruption to the wearer's postural stability or confidence. For example, the controller 106 can detect a vestibular disturbance of the wearer, an occurrence of a fall, an episode of dizziness, an episode of syncope, a seizure, a stroke, an anaphylactic shock, an aneurysm, a hard sit into a chair, a near fall, a trip, a stumble, a change in gait, a hesitation or a fear of falling, or the like.

The optional sensor 104 is adapted to detect a physiological characteristic of the wearer of the body-worn device 102 and generate physiological data representative of the physiological characteristic. Further, the controller is adapted to receive the physiological data from the sensor 104.

The system 100 can include any suitable body-worn device 102 for the wearer that can be worn in any suitable location on the body of the wearer, including but not limited to, a wearable hearing device such as headphones, a wrist-worn device such as a smartwatch, a patch disposed on any portion of a body of the wearer, glasses, etc. The body-worn device can be implanted. The body-worn device can, in one or more embodiments, be integrated into or otherwise disposed in a body part prosthesis, mobility assistance device, or exoskeleton.

Although described as being worn on the body of the wearer, the device 102 can instead be disposed apart from the body of the wearer. For example, the device 102 can be disposed in a room or building and be adapted to monitor one or more individuals proximate to the device using any suitable technique or techniques. In one or more embodiments, the device 102 can utilize at least one of lidar, facial recognition software, camera systems, hazard beacons, Bluetooth-based directional arrival software, geotagging, radio frequency identification (RFID), light sensors and the like to identify and track an individual located in the room or building and provide at least one of physiological data or contextual data regarding the individual to the controller 106 for further processing as is described herein.

In one or more embodiments, the body-worn device 102 can include a hearing assistance device such as behind-the-ear (BTE), in-the-ear (ITE), in-the-canal (ITC), or completely-in-the-canal (CIC) type hearing instrument. It is understood that behind-the-ear type hearing instruments can include devices that reside substantially behind the ear or over the ear. Such devices can include hearing instruments with receivers associated with the electronics portion of the behind-the-ear device, or hearing instruments of the type having receivers in the ear canal of the wearer. Such devices are also known as receiver-in-the-canal (RIC) or receiver-in-the-ear (RITE) hearing devices. In one or more embodiments, the body-worn device 102 can include a cochlear implant (including its processor) or a bone-conduction or otherwise osseointegrated hearing device. It is understood that other body-worn devices not expressly stated herein can fall within the scope of the present subject matter. While depicted as including one body-worn device 102, the system 100 can include two or more body-worn devices. For example, in one or more embodiments, the system 100 can include a left hearing device that is adapted to be acoustically connected to the wearer's left ear and a right hearing device that is adapted to be acoustically connected to the wearer's right ear. In one or more embodiments, the left hearing device can electrically communicate with the right hearing device using any suitable technique or techniques.

Figure 5:
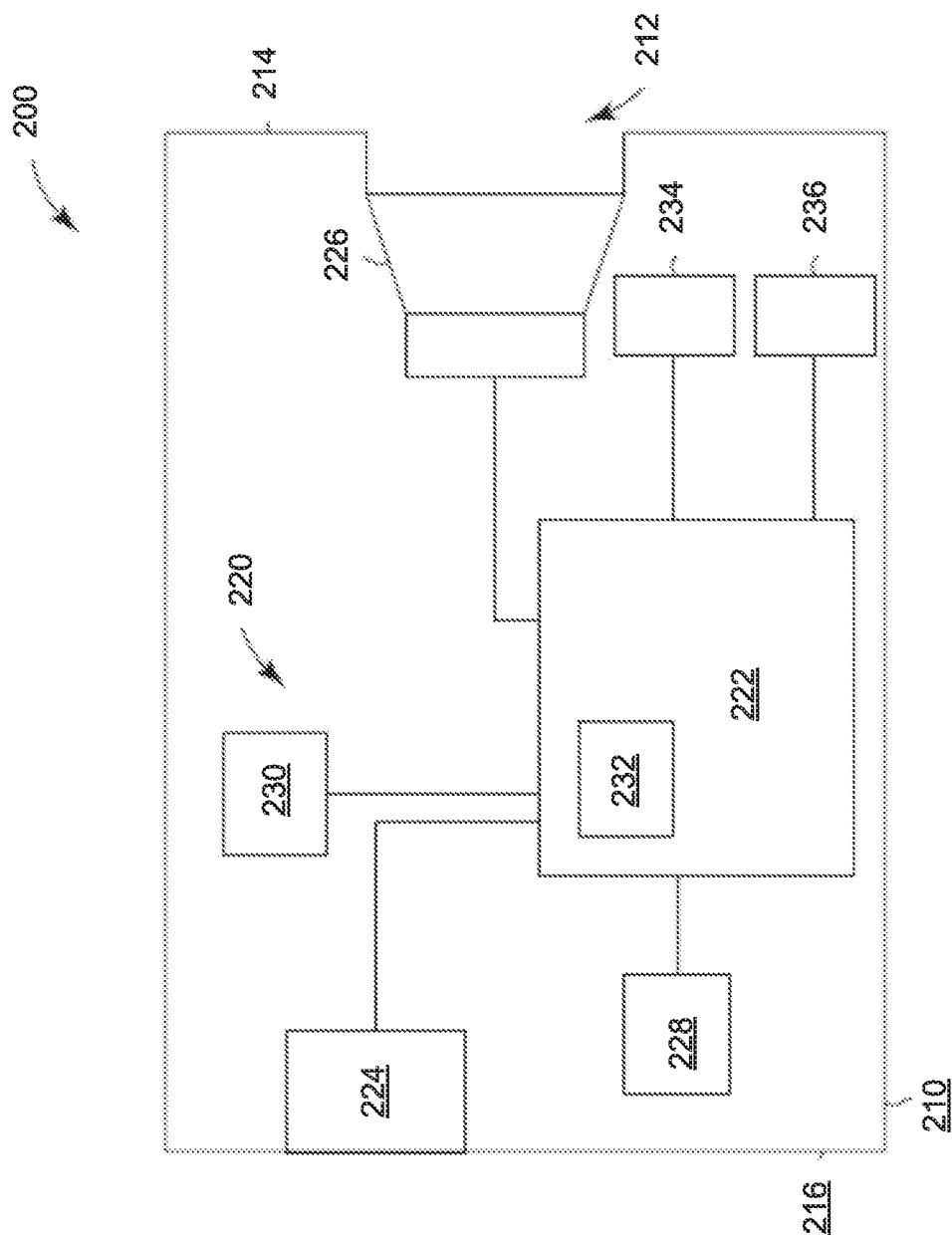
FIG. 5 is a schematic diagram of a body-worn device of the system of FIG. 4.

The body-worn device 102 can include any suitable electronic components or circuitry. In one or more embodiments, the body-worn device 102 includes hearing assistance components. For example, FIG. 5 is a schematic cross-section view of one embodiment of a body-worn device 200. The device 200 includes a housing 210 and hearing assistance components 220 disposed within the housing. Hearing assistance components 220 can include any suitable device or devices, e.g., integrated circuits, power sources, microphones, receivers, etc. For example, in one or more embodiments, the components 220 can include a controller 222 (e.g., controller 106 of FIG. 3), a microphone 224, a receiver 226 (e.g., speaker), a power source 228, an antenna 230, and one or more sensors 234, 236 (e.g., sensor 104 of FIG. 3). The microphone 224, receiver 226, power source 228, antenna 230, and sensors 234, 236 can be electrically connected to the controller 222 using any suitable technique or techniques. In one or more embodiments, the hearing assistance device can be adapted to provide the wearer with auditory information, feedback, or guidance. In one or more embodiments, the hearing assistance device can be adapted to accept verbal or gestural input from the wearer. In one or more embodiments, encephalography (EEG) sensor data can be utilized to infer e.g., the user's intentions.

Any suitable controller 222 can be utilized with the body-worn device 200, e.g., the same controller or controllers described regarding controller 106 of system 100 of FIG. 2. For example, the controller 222 can be adapted to employ programmable gains to adjust the hearing device output to a patient's particular hearing impairment. The controller 222 can be a digital signal processor (DSP), microprocessor, microcontroller, other digital logic, or combinations thereof. The processing can be done by a single processor or can be distributed over different devices. The processing of signals described herein can be performed using the controller 222 or over different devices.

In some embodiments, the controller 222 can be operatively connected to but separate from body-worn or ear-worn device. For example, the controller 222 can be in wireless communication with the body-worn device. Raw sensor data, processed sensor data, or characteristics extracted from sensor data can be transmitted to the operatively-connected controller. Data received by the controller can be collected from one or more devices. In some embodiments, redundant data can increase confidence in the data being collected. In some embodiments, sensor data can be rejected if data is not congruent with other devices or if is determined that a particular device is not actually being worn. Aspects of data collection from multiple devices is provided in U.S. patent application Ser. No. 16/714,339, entitled "HEARING ASSISTANCE SYSTEM WITH ENHANCED FALL DETECTION FEATURES", the content of which is herein incorporated by reference. In some embodiments data collection may be duty-cycled between operatively connected devices to save resources (battery capacity, wireless bandwidth, processing capabilities, etc.).

In one or more embodiments, the controller 222 is adapted to perform instructions stored in one or more memories 232. Various types of memory can be used, including volatile and nonvolatile forms of memory. In one or more embodiments, the controller 222 or other processing devices execute instructions to perform a number of signal processing tasks. Such embodiments can include analog components in communication with the controller 222 to perform signal processing tasks, such as sound reception by the microphone 224, or playing of sound using the receiver 226.

In general, digital hearing devices include a controller or processor. In such devices, programmable gains our audiometric filters can be employed to adjust the hearing device output to a wearer's particular hearing impairment or preferences. The controller 222 (and controller 106 of FIG. 2) can be a digital signal processor (DSP), microprocessor, microcontroller, other digital logic, or combinations thereof. The processing can be performed by a single processor or can be distributed over different devices. The processing of signals referenced in this application can be performed using the processor or other different devices. Processing can be done in the digital domain, the analog domain, or combinations thereof. Processing can be done using subband processing techniques. Processing can be done using frequency domain or time domain approaches. Some processing can involve both frequency and time domain aspects. For brevity, in some examples drawings can omit certain blocks that perform frequency synthesis, frequency analysis, analog-to-digital conversion, digital-to-analog conversion, amplification, buffering, and certain types of filtering and processing. In various embodiments, the processor is adapted to perform instructions stored in one or more memories, which can or cannot be explicitly shown. Various types of memory can be used, including volatile and nonvolatile forms of memory. In various embodiments, the processor or other processing devices execute instructions to perform a number of signal processing tasks. Such embodiments can include analog components in communication with the processor to perform signal processing tasks, such as sound reception by a microphone, or playing of sound using a receiver (i.e., in applications where such transducers are used). In various embodiments, different realizations of the block diagrams, circuits, and processes set forth herein can be created by one of skill in the art without departing from the scope of the present subject matter.

The hearing assistance components 220 can also include the microphone 224 that is electrically connected to the controller 222. Although one microphone 224 is depicted, the components 220 can include any suitable number of microphones. Further, the microphone 224 can be disposed in any suitable location within the housing 210. For example, in one or more embodiments, a port or opening can be formed in the housing 210, and the microphone 224 can be disposed adjacent the port to receive audio information from the wearer's environment.

Any suitable microphone 224 can be utilized. In one or more embodiments, the microphone 224 can be selected to detect one or more audio signals and convert such signals to an electrical signal that is provided to the controller 222. Although not shown, the controller 222 can include an analog-to-digital convertor that converts the electrical signal from the microphone 224 to a digital signal.

Electrically connected to the controller 222 is the receiver 226. Any suitable receiver can be utilized. In one or more embodiments, the receiver 226 can be adapted to convert an electrical signal from the controller 222 to an acoustic output or sound that can be transmitted from the housing 210 to the wearer. In one or more embodiments, the receiver 226 can be disposed adjacent an opening 212 disposed in a first end 214 of the housing 210. As used herein, the term "adjacent the opening" means that the receiver 226 is disposed closer to the opening 212 in the first end 214 than to a second end 216 of the housing 210.

The power source 228 is electrically connected to the controller 222 and is adapted to provide electrical energy to the controller and one or more of the other hearing assistance components 220. The power source 228 can include any suitable power source or power sources, e.g., a battery. In one or more embodiments, the power source 228 can include a rechargeable battery. In one or more embodiments, the components 220 can include two or more power sources 228.

The components 220 can also include the optional antenna 230. Any suitable antenna or combination of antennas can be utilized. In one or more embodiments, the antenna 230 can include one or more antennas having any suitable configuration. For example, antenna configurations can vary and can be included within the housing 210 or be external to the housing. Further, the antenna 230 can be compatible with any suitable protocol or combination of protocols. In one or more embodiments, the components 220 can also include a transmitter that transmits electromagnetic signals and a radio-frequency receiver that receives electromagnetic signals using any suitable protocol or combination of protocols.

For example, in one or more embodiments, the body-worn device 200 (or any other body-worn device described herein) can be connected to one or more external devices using, e.g., Bluetooth, Wi-Fi, magnetic induction, mesh networks, etc. For example, in one or more embodiments, the body-worn device 200 can be wirelessly connected to the Internet using any suitable technique or techniques. Such connection can enable the body-worn device 200 to access any suitable databases, including medical records databases, cloud computing databases, location services, etc. In one or more embodiments, the body-worn device 200 can be wirelessly connected utilizing the Internet of Things (IoT) such that the hearing device can communicate and share data with, e.g., one or more hazard beacons, one or more cameras disposed in proximity to the wearer, motion sensors, room lights, air conditioning and heating controllers, etc. Further, in one or more embodiments, the body-worn device 200 can access weather information via the Internet or a mesh network using any suitable technique or techniques such that the wearer can be informed of potentially hazardous weather conditions.

In one or more embodiments, the body-worn device 200 can include the first sensor 234 and the second sensor 236. Although depicted as including two sensors 234, 236, the body-worn device 200 can include any suitable number of sensors, e.g., 1, 2, 3, 4, 5, or more sensors. The sensors 234, 236 can include any suitable sensor or sensors, e.g., the same sensors described herein regarding sensor 104 of system 100 of FIG. 2. The first sensor 234 can include the same sensor as the second sensor 236. In one or more embodiments, the first sensor 234 includes a sensor that is different from that of the second sensor 236. The sensors 234, 236 can be operatively connected to the controller 222 using any suitable technique or techniques.

In one or more embodiments, first sensor 234 is operatively connected to the body-worn device 200 and adapted to detect a first characteristic of the wearer and generate data (e.g., physiological data or contextual information) representative of the first characteristic. In one or more embodiments, the second sensor 236 is operatively connected to the body-worn device 200 and adapted to detect a second characteristic of the wearer and generate data (e.g., physiological data or contextual information) representative of the second characteristic. The first and second characteristics of the wearer can be any suitable characteristic, e.g., at least one of a physiological characteristic and contextual information of the wearer. The first and second characteristics can include any suitable characteristic, e.g., the same characteristic or characteristics described herein regarding sensor 104 of system 10 of FIG. 4. The first characteristic detected by the first sensor 234 can be the same as or different from the second characteristic detected by the second sensor 236. For example, in one or more embodiments, the first characteristic detected by the first sensor 234 can be eye movement of the wearer and the second characteristic detected by the second sensor 236 can be head movement of the wearer.

Returning to FIG. 4, the sensor 104 is operatively coupled to the body-worn device 102. The sensor 104 can be operatively coupled to the device 102 using any suitable technique or techniques, e.g., electrical, optical, or wireless coupling. The sensor 104 can be disposed in any suitable location. In one or more embodiments, the sensor 104 can be a component of electronic components 220 of the body-worn device 200, e.g., such as sensors 234, 236 of electronic components 220 of FIG. 5. In one or more embodiments, one or more sensors 104 can be disposed outside of the housing of the body-worn device 102 and operatively coupled to the device and the controller 106 using any suitable technique or techniques. In one or more embodiments, one or more sensors 104 can be disposed within one or both ears and outside the ear of the wearer. In one or more embodiments, one or more sensors 104 can be disposed within one or more devices worn by one or more individuals other than the subject of interest. In one or more embodiments, one or more sensors 104 can be disposed within one or more physical hazard beacons, e.g., as described in U.S. Patent Publication No. 2018/0233018 A1, entitled FALL PREDICTION SYSTEM INCLUDING A BEACON AND METHOD OF USING SAME.

The sensor 104 can include any suitable sensor or sensors. For example, the sensor 104 can include at least one of an accelerometer, barometer, gyroscope, heart rate sensor, blood pressure sensor, magnetometer, eye sensor, EEG sensor, blood sugar sensor, light sensor, sweat sensor, pupillometry sensor, cerumen sensor, cortisol sensor, body temperature sensor, humidity sensor, air quality sensor, and combinations thereof. The sensor 104 can be adapted to detect any suitable characteristic of the wearer, e.g., at least one of a physiological characteristic and a contextual characteristic of the wearer.

Further, in one or more embodiments, the sensor 104 can be adapted to detect one or more contextual characteristics proximate to the wearer of the body-worn device 102. For example, such sensor 104 can include at least one of an ambient temperature sensor, barometer, microphone, GPS sensor, moisture/humidity sensor, image sensor (i.e., a camera), and combinations thereof.

Operatively connected to the body-worn device 102 is the controller 106. In one or more embodiments, the controller 106 can also be operatively connected to the sensor 104. The controller 106 can include any suitable controller or controllers, e.g., the same controller described regarding controller 222 of the body-worn device 200 of FIG. 5. The controller 106 can be disposed in any suitable location relative to the body-worn device 102 and the sensor 104. In one or more embodiments, the controller 106 is disposed within the housing of the body-worn device 102, e.g., within housing 210 of body-worn device 200 of FIG. 4. In one or more embodiments, the controller 106 can be disposed external to the body-worn device 102, e.g., the body-worn device can be wirelessly connected to the wearer's smartphone, computer, or the cloud using any suitable technique or techniques. In one or more embodiments, the controller 106 can include a first controller disposed within the body-worn device 102 and one or more additional controllers disposed externally to the body-worn device.

The predictive fall event management system 100 can be utilized to receive input information and determine the likelihood or probability that the wearer of the fall prediction system will fall. In one or more embodiments, the system 100 can be utilized to receive input information from any suitable source to determine whether the wearer has fallen. The input information can be provided using any suitable sensor, device, or database. For example, the input information can be provided to the controller 106 by the sensor 104, the body-worn device 102, manually by one or more of the wearer, a caregiver, and a medical professional, or obtained from other systems via wired or wireless connections to system 100 and/or to cloud-based data server.

Further, the predictive fall event management system 100 can provide any suitable outputs that can be based on the probability of a fall or that a fall has occurred. Any suitable output or outputs can be provided by the system 100, e.g., notifications, reports, IoT triggers (e.g., activating room lighting), treatments to the wearer of the device 102, etc. In one or more embodiments, the system 100 can be utilized to detect head impact, check with the wearer for consciousness, and inform one or more of the wearer, caregiver, and medical professional of the detection of a head impact and level of consciousness of the wearer.

Figure 6:
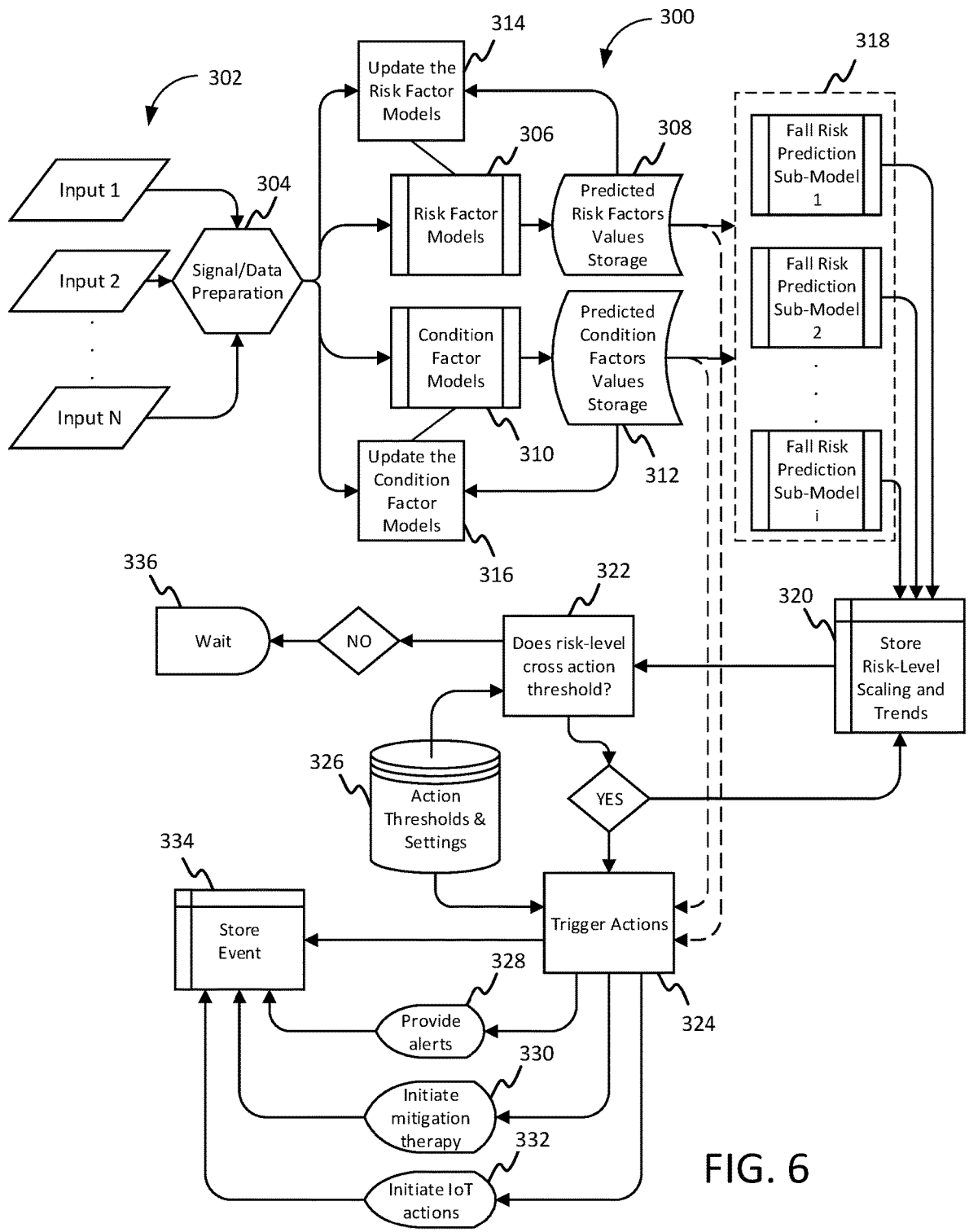
FIG. 6 is a flowchart of one embodiment of a method that can be utilized with the predictive fall event management system.

The fall prediction system 100 can utilize any suitable technique or techniques to determine the risk of a fall and/or that a fall has occurred. For example, FIG. 6 is a flowchart of one embodiment of method 300 for predicting and detecting a fall. The method 300 can be implemented using any suitable device or system, e.g., predictive fall event management system 100 of FIG. 3. Although described in reference to predictive fall event management system 100 of FIG. 3, the method 300 can be utilized with any suitable device or system. In one or more embodiments, controller 106 system 100 of FIG. 3 can be adapted to perform method 300. Further, the controller 106 can be adapted to perform the method 300 through firmware, software, etc. In one or more embodiments, the controller 106 can be or include an application-specific integrated circuit (ASIC) that includes the method 300.

Method 300 includes receiving inputs 302 at 304 for data preparation. Any suitable inputs 302 can be received. In one or more embodiments, inputs 302 can include physiological data representative of a physiological characteristic of the wearer of the body-worn device 102 over a monitoring time period. Further, inputs 302 can include contextual data representative of context information of the wearer over the monitoring time period. Medical/health reports regarding the wearer can also be provided as inputs 302. Any suitable databases containing, e.g., calendar data, reminder data, and data relative to actions of an artificial intelligence can also be provided as inputs 302. Further, group data from the cloud can also be provided as inputs at 302.

Such data can be prepared at 304 utilizing any suitable technique or techniques. In one or more embodiments, data from inputs 302 can be, e.g., filtered, time stamped, assigned metadata memory locations, and combinations thereof, at 304. As used herein, the term "data" can include a single datum or a plurality of data values or statistics. The term "statistics" can include any appropriate mathematical calculation or metric relative to data interpretation, e.g., probability, confidence interval, distribution, range, or the like.

At 306, one or more physiological risk factor models can receive the physiological data from inputs 302 and provide to storage 308 one or more outputs of risk factor values or statistics of a fall by the wearer based on the physiological data. The physiological risk factor models can utilize any suitable technique or techniques to determine physiological risk factor values or statistics at 306. Similarly, contextual data inputs 302 can be received by contextual factor models at 310. The contextual factor models 310 can provide to storage 312 one or more outputs of contextual risk factor values or statistics of a fall by the wearer based upon contextual data. The contextual factor models 310 can utilize any suitable technique or techniques to provide contextual factor values or statistics.

Further, one or more future physiological states or contextual states based at least in part one or more of the physiological data and contextual data can also be determined at 306 and 310, and then stored at 308 and 312 respectively. Any suitable technique or techniques can be utilized to determine the future physiological states and future contextual states. One or more pattern recognition machine learning techniques such as Hidden Markov Models (HMMs), Bayesian models, non-linear regressions, decision trees, support vector machines, neural networks, etc. can be applied to input data 302 to predict future physiological and contextual states based upon, at least in part, one or more of present and historical data. During a learning stage, prepopulated group data or laboratory data can be utilized to form the basis of training one or more pre-trained models. As the system collects data about the user over time, one or more of these models can be updated using any suitable training techniques.

For example, a particular model at 306 can be trained or continuously adapted at 314 to learn the effects that a specific medication has on an individual, over time, based on data from a group of individuals. The model can be further updated, for a specific user, as specific data relative to the severity and timing of any observable changes to the user is collected. In this example, an observable change can relate to one or more characteristics of the user's gait and postural stability that can be observed or monitored using any suitable sensor arrangement. In one or more embodiments, the time at which the user will ingest a particular medication can be predicted based upon any suitable contextual data e.g., historical, physiological, or historical contextual data, scheduled reminders, push notifications, location information, etc. Further, a particular model at 310 can be trained or continuously adapted at 316 based on an individual's historical environment and location data, over time, to recognize patterns such that a prediction of the individual's future location can be made at 310. Historical fall event and balance event data from one or more of the individual or a group of individuals, at a given location, can further inform the risk factor associated with the location the individual is predicted to be at in a future time.

The physiological risk factor models 306 can be updated at 314 based upon one or more of the inputs 302 and the physiological risk factor values or statistics. For example, changes in gait such as increased postural sway, irregular stride, lower foot clearance, and decreased walking speed can be detected, using any suitable means, and can indicate that a new lower limb limitation can increase the individual's risk for stumbling over uneven walking paths.

The contextual factor models 310 can also be updated at 316 based upon one or more of the inputs 302 and the contextual risk factor values or statistics. For example, changes in weather conditions or geographical locations of the wearer can be factored into the contextual factor models 310 using any suitable technique or techniques.

In one or more embodiments, the method 300 includes receiving balance data representative of a balance event and updating a fall risk model based upon one or more of the physiological data, contextual data, and the balance data. The balance data can be an input 302 and provided as an output from the signal/data preparation at 304 to the physiological factor models at 306. Balance events can include a vestibular disturbance of the wearer, an occurrence of a fall, an episode of dizziness, an episode of syncope, a seizure, a stroke, an anaphylactic shock, an aneurysm, a hard sit into a chair, a near fall, a trip, a stumble, a change in gait, a fear of falling, or the like of the wearer of the body-worn device 102. Such balance, fall, and positional data can also be utilized at 314 to update the physiological factor models at 314. As a result, the controller 106 can be adapted to detect disruption to an individual's postural stability, e.g., a fall or other balance event (temporary instability) using any suitable technique or techniques.

At 318, at least one of the physiological risk factor statistics and contextual risk factor statistics can be provided to one or more fall risk prediction sub-models at 318. One or more fall risk statistics could be provided for one or more future moments in time. Any suitable technique or techniques can be utilized with the one or more fall risk prediction sub-models 318. In one or more embodiments, multiple fall risk statistics models can be produced at 318 that is contingent upon the occurrence of one or more predicted contextual factors. For example, the individual's fall risk statistics can be different if they decided to either stand up or remain seated. In one or more embodiments, the individual can be informed regarding one or more predicted fall risk statistics such that the individual understands the predicted consequences of one or more predicted actions that they may take. Further, the sub-models 318 can be adapted to determine a future fall risk value based upon the one or more future physiological states or contextual states using any suitable technique or techniques. The sub-model can be further trained or continuously adapted based on the historical fall event and balance event data from one or more of the individual or a group of individuals.

In one or more embodiments, the sub-models 318 can generate a risk or probability value of a fall that can be based on a predetermined formula or formulas that can be derived from experimental data. The formula can also be entirely learned or modified through various machine learning approaches. For example, when a fall event is detected, the method 300 can send postural data collected before the event by one or more sensors 104, e.g., to a cloud server. In one or more embodiments, data from the wearer and other wearers can be used to train a regression model or deep neural network to estimate the risk of a fall for an individual wearer at 318. One or more of the sub-models 318 can be generated from analytics or machine learning of larger group data using any suitable technique or techniques, e.g., regression, steady-state, Bayesian, classification trees, Volterra, support vector machine, Gaussian mixture, neural network techniques, and combinations thereof.

The sub-models 318 can provide an estimate or probability of the general risk (or capability of keeping balance) of the wearer and learn the wearer's norms regarding motion patterns and health/physiological information. Inputs for generating the sub-models 318 can either be obtained based on clinical evaluations and medical history or be learned by the predictive fall event management system 100 from one or more inputs provided by various types of sensors, e.g., sensor 104 and responses to queries.

For example, motion patterns of the wearer and changes to such patterns can be estimated and monitored based on the outputs from one or more of an inertial measurement unit (IMU) sensor, GPS sensor barometer, magnetometer, EEG sensor, camera, etc. The motion of the wearer can include sway amplitude and speed while walking, speed and trajectory when sitting down or standing up, speed and radius when turning, stride length, symmetry and variance, frequency of walks, length or distance of walks, reaction speed, etc.

In one or more embodiments, one or more of periodic assessments of functional balance ability, muscle strength, perceived balance efficacy, fear of falling, or functional reaction speed of the user can be performed by the system 100 and queried to the user or a third party. In one or more embodiments, one or more of results of periodic functional balance ability, muscle strength, perceived balance efficacy, fear of falling, or functional reaction speed of the user can be entered into the system 100 manually by either the user or a third party. As an illustrative example, the results of e.g., the Timed Up and Go (TUG) test can be calculated either by the instrumented body-worn device or entered by the individual or a third-party observer.

In one or more embodiments, physiological data that can be provided as inputs to the sub-models 318 include heart rate, blood pressure, blood sugar, blood oxygen, core body temperature, etc., and can be monitored utilizing any suitable sensor or sensors 104. All such inputs and how they change over time can be monitored and used to estimate whether a fall condition is satisfied (i.e., how prone the wearer is to a fall).

For example, one of the sub-models 318 can evaluate postural stability (i.e., displacement of the head of the wearer in three dimensions) of the wearer to determine a fall risk value based on monitoring of the wearer at 306. Any suitable sensor or sensors 104 can be utilized to determine postural stability, e.g., one or more of an accelerometer, gyroscope, microphone, barometer, optical sensor, and bio-electrical sensor. In one or more embodiments, the sensor 104 can include an accelerometer and a gyroscope as the primary sensors for postural balance and fall-risk monitoring and the other sensors can be secondary sensors. For example, a secondary sensor can include a microphone that can be used for detecting foot-falls or a fall event. Further, a barometer can be used to detect stair climbing. In addition, an optical sensor can be used for measuring heart rate and other biosignals. A bioelectric sensor can be used for monitoring electro-, cardio-, encephalo-, occulo-, and myo-graph signals from any location on the head and body of the wearer.

In general, there can be multiple activities and postures during which one may fall down, most commonly walking and standing, transitions between postures such as movement between standing and sitting, etc. Further, there can be identifiable physiological events that precede the fall, such as postural hypotension.

One or more physiological sensors 104 can be employed to identify a "prodrome" of a postural instability. Some possible techniques of using this sensor information for this purpose can be used individually or in combination.

For example, in one or more embodiments, the sensor 104 can include one or more of an accelerometer and a gyroscope. Signals form the sensor 104 can be used to compute and monitor a deviation from a stable position and a velocity with which that takes place. In one or more embodiments, the controller 106 can utilize the signal inputs from the sensor 104 to generate a measure of postural stability. Such postural stability can be included in one or more physiological data inputs at 302. Postural stability can be recorded during normal daily activities, including standing, walking, and climbing stairs. Postural stability can also be recorded during structed activities and functional tests, e.g., during performance of a TUG test or the like. A threshold of normal stability can be established based on clinical postural stability testing or during a user-initiated initialization involving one or more of these activities. Measurements in case of a recorded fall can be used to adjust the threshold, if appropriate.

Acceleration of the head of the wearer while walking is complex, with the most prominent feature in the unprocessed accelerometer signal being that of the footfall. Adding to this complexity can be stabilization of the head by the neck. Footfall signals can be diminished by neck stabilization but still can be detectable. Vestibular-ocular reflexes can also be measured as the eye will attempt to stabilize the individual's visual field with each step. In one or more embodiments, head oscillation in three dimensions (antero-posterior (AP), lateral, and vertical) can measured. Components of the displacement and the velocity in each dimension can be computed as measures of the postural stability. Although generally correlated and constrained by the body, the head can move relatively independently, which introduces artifacts. To mitigate these artifacts, in one or more embodiments, the velocity and displacement of the head oscillation are computed only when the pitch, yaw and/or roll motions of the head a slower than some predefined thresholds. Artifacts related to head movements can also be mitigated, by the controller, through the integration of sensor inputs of body-worn sensors placed on the chest, trunk, waist, etc. The values or statistics can depend upon the speed and type of body movement.

In one or more embodiments, the controller 106 can be adapted to determine a fall condition by measuring a maximum displacement between a longitudinal axis of the wearer and a normal to the earth's surface as a function of time. Further, in one or more embodiments, the controller 106 can be adapted to determine the fall condition by measuring a maximum velocity of displacement between a longitudinal axis of the wearer and a normal to the earth's surface.

Fall risk thresholds related to safe postural stability or limits of stability can be established by balance testing in a clinical setting or by user-conducted or self-directed tests. A fall risk signal or other fall risk output can be generated based on single or multiple threshold crossings.

Parameters of postural stability, i.e., balance metrics, and fall risk values or statistics can be of interest to one or more of the wearer, caregivers such as the family members, and medical professionals. Balance metrics and fall risk values or statistics can be monitored e.g., daily or hourly and transmitted to various parties. The system can continuously monitor the user and once a fall risk threshold is exceeded, a fall risk output such as a discrete audio alert can be provided to the user.

In laboratory conditions, head worn IMU sensors can be utilized to characterize small motions (e.g., sway) that can be important for balance evaluation. The orientation of the IMU sensors, however, is highly controlled and well calibrated in the laboratory. In practice, when wearers are wearing two hearing devices, proper alignment of the IMU sensors at each side of the head is desired. Any suitable technique or techniques can be utilized to align the sensor 104 in both left and right hearing devices of the system 10, e.g., the techniques described in U.S. patent application Ser. No. 15/331,230, filed Oct. 21, 2016, and entitled HEAD RELATED TRANSFER FUNCTION INDIVIDUALIZATION FOR HEARING DEVICE. In one or more embodiments, a technique can be utilized to compensate for the orientation mismatch between two hearing devices so that the IMU sensors on both sides of the head can be collaboratively aligned with the head orientation and used to derive postural stability information.

In one or more embodiments, the fall risk value based upon postural stability can be determined by first detecting that the wearer is walking. One or more artifacts from the sensor 104 caused by foot-impact can be filtered out using any suitable technique or techniques. Postural stability can be determined using any suitable technique or techniques. Velocity components of such postural stability can be determined using any suitable technique or techniques. In one or more embodiments, the fall risk value can be based upon walking speed, distance walked, frequency of walks, duration of walks, frequency of successful postural transitions, speed of postural transitions, or the like and other activity classifications, and combinations thereof.

A composite sensitivity parameter of the contribution of the sensor 104 (e.g., one or more accelerometers) to the overall fall risk value or statistic can be determined using any suitable technique or techniques. In one or more embodiments, the sensitivity of the fall risk value or statistics to an amplitude of the postural stability can be determined using, e.g., one or more of a user input after a near-fall event, a balance study, and fall detection. The sensitivity of the fall risk value or statistics to the stability velocity at a pre-determined postural stability can be determined using, e.g., one or more user inputs after a near-fall event, a balance test, fall detection or the like. Further, the sensitivity of the fall risk value to a statistically determined combination of the postural stability and the stability velocity can also be determined.

In one or more embodiments, postural stability, sway velocity and other posture, walking and fall-related information can be routinely transmitted to healthcare professionals. The wearer's posture while standing and walking, actual fall events, and user-indicated near-fall events can also be transmitted to healthcare professionals.

If the fall risk value or statistics crosses a fall risk threshold, then an alert can be sent to one or more of the wearer, caregiver, and medical professional. Such alerts can include instructions for how to prevent a fall from occurring.

In one or more embodiments, sensors 104 having one or more accelerometers can be placed in both ears of the wearer. Acceleration of the mid-point between the two ears, as opposed to that of one ear, can be calculated to determine postural stability. Further, false positives of fall detection can be reduced by ensuring both sensors 104 follow the same nominal motion pattern. In addition, head rotation around the vertical axis i.e., the yaw, can also be determined and utilized to calculate the fall risk value.

In one or more embodiments, a fall condition can be determined by measuring eye movement of the wearer. For example, the fall prediction system 100 can detect eye movements and compare such eye movements to a baseline to determine whether a vestibular event is occurring that can increase the risk of fall. The sensor 104 of the predictive fall event management system 100 can include one or more eye movement sensors. In one or more embodiments, the system 100 can also include one or more sensors 104 that can measure head movement of the wearer. Data from such head movement sensors 104 can be utilized to correlate with eye movement sensor data to determine the risk of a fall. Any suitable fall prediction system or device can be utilized to measure eye movement of a wearer, e.g., the devices described in U.S. Pat. No. 9,167,356, issued Oct. 20, 2015, and entitled ELECTROOCULOGRAM AS A CONTROL IN A HEARING ASSISTANCE DEVICE.

For example, in one or more embodiments, one or more inputs can be provided by one or more of the wearer, the caregiver, and the physician. For example, one or more inputs can be provided by the wearer in response to one or more queries provided, e.g., by the body-worn device 102 (or ear-worn device or hearing device), the caregiver, or the physician.

In one or more embodiments, one or more of the sub-models 318 can evaluate eye movement of the wearer to determine a fall risk value based on monitoring of the wearer at 306. For example, the system 100 can detect eye movements and compare such eye movements to a baseline to determine whether a vestibular event is occurring that can increase the risk of fall. The sensor 104 of the fall prediction system 100 can include one or more eye movement sensors. In one or more embodiments, the system 100 can also include one or more sensors 104 that can measure head movement of the wearer. Data from such head movement sensors 104 can be utilized to correlate with eye movement sensor data to determine the risk of a fall. Any suitable system or device can be utilized to measure eye movement of a wearer, e.g., the devices described in U.S. Pat. No. 9,167,356, issued Oct. 20, 2015, and entitled ELECTROOCULOGRAM AS A CONTROL IN A HEARING ASSISTANCE DEVICE.

In one or more embodiments, data from eye movement sensors (e.g., Electrooculography (EOG) sensors) and positional sensors (collectively sensors 104 of FIG. 4) can be utilized for early detection of peripheral vestibular asymmetry (which generally cause nystagmus and feelings of imbalance/dizziness to occur). Nystagmus is an involuntary oscillation of one or both eyes about one or more axes. The eye movement sensors can allow the system 100 to make one or more of the following determinations: (a) whether or not the nystagmus is typical given the wearer's baseline movement data, (b) whether the wearer's visual pursuits are smooth or otherwise atypical. Other sensors can be utilized with the method 300 to predict and/or detect falls. For example, the system 100 can include at least one of a microphone and an ambient light sensor. Any suitable technique or techniques can be utilized to determine a fall risk value utilizing eye movement sensors, e.g., the techniques described in U.S. Patent Publication No. 2018/0228404 A1, entitled FALL PREDICTION SYSTEM AND METHOD OF USING SAME.

Outputs from the fall risk prediction sub-models 318 can be stored at 320. Such outputs can include data that includes risk-level scaling and trends. At 322 a determination, for a future time, of whether a fall condition is satisfied can be made based upon the one or more future physiological states or context states. Any suitable technique or techniques can be utilized at 322 to determine whether a fall condition has been satisfied. For example, reinforcement learning techniques at 324 can be applied to select the best possible output behavior strategy in a given situation. Reinforcement learning models can consider one or more of a predicted physiological risk factor, predicted contextual risk factor, historical physiological risk factor, historical contextual factor, predicted fall event, historical fall event, predicted balance event, historical balance events, and the like. In one or more embodiments, the reinforcement learning model can further consider the fall risk statistics associated with historical data to optimize one or more of the present and future fall prevention outputs at 324. In one or more embodiments, determining whether the fall condition is satisfied at 322 includes applying a future fall risk value to a fall risk model. Such fall risk model can be developed from outputs from the fall risk prediction sub-models 318. In one or more embodiments, the system 100 can include several models: a physiological model, a contextual model, and a fall risk model. The fall risk model can use the output (e.g., state) of the physical model and contextual model as inputs to the fall risk model. The future fall risk value can be based upon the one or more future physiological states or contextual states. In one or more embodiments, the controller 106 can be adapted to determine at 322, for each of a plurality of future times, whether an anticipated fall condition is satisfied based upon one or more of the physiological data and contextual data. Further, in one or more embodiments, the controller 106 can be adapted to determine at 322, for a plurality of future times, whether an anticipated fall condition is satisfied based upon a combination of the physiological data and the contextual data. In one or more embodiments, the controller 106 can be adapted to determine at 322, for a plurality of future times, whether the fall condition is satisfied by determining a future fall risk value based upon the one or more future physiological states or contextual states.

Data related to fall conditions including thresholds can be stored at 326 and utilized at 322 to determine whether the fall condition has been satisfied at 322 and also utilized to generate fall prevention outputs at 324.

If the fall condition has been met at 322, then the method 300 proceeds to 324, where a fall prevention output responsive to satisfaction of the fall condition is generated. The fall prevention output can include one or more outputs described herein. For example, the fall prevention output can include one or more alerts that are provided to one or more of the wearer, caregiver, and medical professional for proper diagnosis and treatment at 328. Further, for example, a fall prevention output can include initiating mitigation therapy at 330. Such mitigation therapy can include initiating a balance training regimen or corrective measure as described, e.g., in U.S. Patent Publication No. 2018/0317837A1, entitled HEARING ASSISTANCE DEVICE INCORPORATING VIRTUAL AUDIO INTERFACE FOR THERAPY GUIDANCE. In one or more embodiments, the fall prevention output can include delivery or modification of a therapy or initiation of an intervention, e.g., activation of an exoskeleton worn by the wearer. Further, the fall prevention output can include generating an IoT action at 332 such as sending one or more signals to one or more IoT devices proximate to the wearer to help prevent the fall or otherwise protect the wearer from injury, increasing an intensity of the ambient light for the wearer's environment, etc.

A particular instance of when the fall condition is satisfied at 322 and which fall prevention outputs are generated at 324 can be stored at 334. Such data that is stored at 334 can be utilized to updated one or both of the physiological factor models at 314 or the contextual factor models at 316. Further, such data of a fall condition being met can be utilized to modify one or more of the fall risk prediction sub-models at 318.

If the fall condition has not been satisfied at 322, then the method 300 proceeds to a wait condition at 336.

Further Embodiments

In a first aspect, a predictive fall event management system, is included having a body-worn device, and a controller operatively connected to the body-worn device, wherein the controller is adapted to: receive one or more of physiological data representative of a physiological characteristic of a wearer of the body-worn device over a monitoring time period, and contextual data representative of context information of the wearer over the monitoring time period, determine one or more future physiological states or contextual states based at least in part on one or more of the physiological data and the contextual data, determine, for a future time, whether a fall condition is satisfied based upon the one or more future physiological states or contextual states, and generate a fall prevention output responsive to satisfaction of the fall condition.

In a second aspect, in addition to one or more of the preceding or following aspects, or in the alternative to some aspects, the system further can include a sensor operatively connected to the body-worn device and adapted to detect the physiological characteristic of the wearer of the body-worn device and generate the physiological data representative of the physiological characteristic, wherein the controller is adapted to receive the physiological data from the sensor.

In a third aspect, in addition to one or more of the preceding or following aspects, or in the alternative to some aspects, the controller is further adapted to determine, for each of a plurality of future times, whether an anticipated fall condition is satisfied based upon one or more of the physiological data and the contextual data.

In a fourth aspect, in addition to one or more of the preceding or following aspects, or in the alternative to some aspects, the controller is further adapted to determine, for a plurality of future times, whether an anticipated fall condition is satisfied based upon a combination of the physiological data and the contextual data.

In a fifth aspect, in addition to one or more of the preceding or following aspects, or in the alternative to some aspects, the controller is further adapted to determine, for a future time, whether the fall condition is satisfied by determining one or more of a future fall risk value and statistics based upon the one or more future physiological states or contextual states.

In a sixth aspect, in addition to one or more of the preceding or following aspects, or in the alternative to some aspects, wherein determining whether the fall condition is satisfied includes applying one or more of the fall risk value and statistics to a fall risk model.

In a seventh aspect, in addition to one or more of the preceding or following aspects, or in the alternative to some aspects, the controller is further adapted to: receive balance data representative of a balance event, and update the fall risk model based upon one or more of the physiological data, contextual data, and the balance data.

In an eighth aspect, in addition to one or more of the preceding or following aspects, or in the alternative to some aspects, physiological data includes at least one of a determined fall risk, inertial sensor data, heart rate information, blood pressure information, drug concentration information, blood sugar level, body hydration information, neuropathy information, blood oximetry information, hematocrit information, body temperature, cortisol levels, age, sex, gait or postural stability attribute, vision, eye movement, or head movement.

In a ninth aspect, in addition to one or more of the preceding or following aspects, or in the alternative to some aspects, physiological data includes one or more inputs provided by the wearer in response to one or more queries.

In a tenth aspect, in addition to one or more of the preceding or following aspects, or in the alternative to some aspects, contextual data includes at least one of weather condition, environmental condition, sensed condition, location, velocity, acceleration, direction, hazard beacon, type of establishment occupied by the wearer, camera information, or presence of stairs.

In an eleventh aspect, in addition to one or more of the preceding or following aspects, or in the alternative to some aspects, the fall prevention output includes one or more of an alert provided to the wearer, electrical stimulation, and thermal stimulation, wherein the alert includes one or more of an audible alert, a visual alert, or a tactile alert.

In a twelfth aspect, in addition to one or more of the preceding or following aspects, or in the alternative to some aspects, the fall prevention output includes a modification of an environmental context of the wearer.

In a thirteenth aspect, in addition to one or more of the preceding or following aspects, or in the alternative to some aspects, the fall prevention output includes transmission of one or more of the physiological data and the contextual data to one or more of a caregiver, a medical professional, a database, or the wearer.

In a fourteenth aspect, in addition to one or more of the preceding or following aspects, or in the alternative to some aspects, the controller is further adapted to detect disruption to the wearer's postural stability.

In a fifteenth aspect, a method is included, the method including receiving one or more of physiological data representative of a physiological characteristic of a wearer of the body-worn device over a monitoring time period, and contextual data representative of context information of the wearer over the monitoring time period, determining one or more future physiological states or contextual states based at least in part on one or more of the physiological data or the contextual data, determining, for a future time, whether a fall condition is satisfied based upon one the one or more future physiological states or contextual states, and generating a fall prevention output responsive to satisfaction of the fall condition.

In a sixteenth aspect, in addition to one or more of the preceding or following aspects, or in the alternative to some aspects, a method further can include determining, for a plurality of future times, whether an anticipated fall condition is satisfied based upon one or more of the physiological data and the contextual data.

In a seventeenth aspect, in addition to one or more of the preceding or following aspects, or in the alternative to some aspects, a method further can include determining, for a plurality of future times, whether an anticipated fall condition is satisfied based upon a combination of the physiological data and the contextual data.

In an eighteenth aspect, in addition to one or more of the preceding or following aspects, or in the alternative to some aspects, a method further can include: receiving balance data representative of a balance event, and updating the fall risk model based upon one or more of the physiological data, contextual data, and the balance data.

In a nineteenth aspect, in addition to one or more of the preceding or following aspects, or in the alternative to some aspects, determining whether a fall condition is satisfied includes applying one or more of the fall risk value and statistics to a fall risk model.

In a twentieth aspect, in addition to one or more of the preceding or following aspects, or in the alternative to some aspects, determining whether a fall condition is satisfied includes determining one or more of a future fall risk value and statistics based upon the one or more future physiological states or contextual states.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example can be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

The invention claimed is:

1. A predictive fall event management system, comprising:
   a body-worn device; and
   a controller operatively connected to the body-worn device, wherein the controller is adapted to:
      receive one or more of
         physiological data representative of a physiological characteristic of a wearer of the body-worn device over a monitoring time period; and
         contextual data representative of context information of the wearer over the monitoring time period;
      determine a first future physiological state or a first contextual state based at least in part on one or more of the physiological data and the contextual data at a first future time, wherein the first future time is between five seconds and five minutes in the future;
      determine a second future physiological state or a second contextual state based at least in part on one or more of the physiological data and the contextual data at a second future time wherein the second future time is at least ten minutes in the future;
      determine, for the first future time, whether a fall condition is satisfied based upon the first future physiological state or the first contextual state;
      determine, for the second future time, whether the fall condition is satisfied based upon the second future physiological state or the second contextual state;
      generate a fall prevention output responsive to satisfaction of the fall condition for the first future time and the second future time.

2. The system of claim 1, further comprising a sensor operatively connected to the body-worn device and adapted to detect the physiological characteristic of the wearer of the body-worn device and generate the physiological data representative of the physiological characteristic, wherein the controller is adapted to receive the physiological data from the sensor.

3. The system of claim 1, wherein the controller is further adapted to determine, for the first future time and the second future time, whether an anticipated fall condition is satisfied based upon a combination of the physiological data and the contextual data.

4. The system of claim 1, wherein the controller is further adapted to determine, for the first future time and the second future time, whether the fall condition is satisfied by determining one or more of a future fall risk value and statistics based upon the one or more future physiological states or contextual states.

5. The system of claim 4, wherein determining whether the fall condition is satisfied includes applying one or more of the fall risk value and statistics to a fall risk model.

6. The system of claim 5, wherein the controller is further adapted to:
   receive balance data representative of a balance event; and
   update the fall risk model based upon one or more of the physiological data, contextual data, and the balance data.

7. The system of claim 1, wherein physiological data comprises at least one of a determined fall risk, inertial sensor data, heart rate information, blood pressure information, drug concentration information, blood sugar level, body hydration information, neuropathy information, blood oximetry information, hematocrit information, body temperature, cortisol levels, age, sex, gait or postural stability attribute, vision, eye movement, or head movement.

8. The system of claim 1, wherein physiological data comprises one or more inputs provided by the wearer in response to one or more queries.

9. The system of claim 1, wherein contextual data comprises at least one of weather condition, environmental condition, sensed condition, location, velocity, acceleration, direction, hazard beacon, type of establishment occupied by the wearer, camera information, or presence of stairs.

10. The system of claim 1, wherein the fall prevention output comprises one or more of
    an alert provided to the wearer;
    electrical stimulation; and
    thermal stimulation;
    wherein the alert comprises one or more of an audible alert, a visual alert, or a tactile alert.

11. The system of claim 1, wherein the fall prevention output comprises a modification of an environmental context of the wearer.

12. The system of claim 1, wherein the fall prevention output comprises transmission of one or more of the physiological data and the contextual data to one or more of a caregiver, a medical professional, a database, or the wearer.

13. The system of claim 1, wherein the controller is further adapted to detect disruption to the wearer's postural stability.

14. The system of claim 1, wherein the second future time is at least 72 hours in the future.

15. A method comprising:
    receiving one or more of
       physiological data representative of a physiological characteristic of a wearer of the body-worn device over a monitoring time period; and
       contextual data representative of context information of the wearer over the monitoring time period;
    determining a first future physiological state or a first contextual state based at least in part on one or more of the physiological data and the contextual data at a first future time, wherein the first future time is between five seconds and five minutes in the future;
    determining a second future physiological state or a second contextual state based at least in part on one or more of the physiological data and the contextual data at a second future time wherein the second future time is at least ten minutes in the future;
    determining, for the first future time, whether a fall condition is satisfied based upon the first future physiological state or the first contextual state;
    determining, for the second future time, whether the fall condition is satisfied based upon the second future physiological state or the second contextual state;
    generating a fall prevention output responsive to satisfaction of the fall condition for the first future time and the second future time.

16. The method of claim 15, further comprising determining, for the first future time and the second future time, whether an anticipated fall condition is satisfied based upon a combination of the physiological data and the contextual data.

17. The method of claim 15, further comprising:
    receiving balance data representative of a balance event; and
    updating the fall risk model based upon one or more of the physiological data, contextual data, and the balance data.

18. The method of claim 15, wherein determining whether a fall condition is satisfied includes applying one or more of the fall risk value and statistics to a fall risk model.

19. The method of claim 18, wherein determining whether a fall condition is satisfied includes determining one or more of a future fall risk value and statistics based upon the one or more future physiological states or contextual states.

20. The method of claim 15, wherein the second future time is at least 72 hours in the future.

\* \* \* \* \*